United States Patent
Nagaoka et al.

(10) Patent No.: US 7,103,139 B2
(45) Date of Patent: Sep. 5, 2006

(54) X-RAY CT DEVICE AND IMAGE DISPLAYING METHOD THEREFOR

(75) Inventors: Takayuki Nagaoka, Sakura (JP); Osamu Miyazaki, Moriya (JP)

(73) Assignee: Hitachi Medical Corporation, Tokyo (JP)

( * ) Notice: Subject to any disclaimer, the term of this patent is extended or adjusted under 35 U.S.C. 154(b) by 221 days.

(21) Appl. No.: 10/468,711

(22) PCT Filed: Mar. 8, 2002

(86) PCT No.: PCT/JP02/02190

§ 371 (c)(1),
(2), (4) Date: Aug. 22, 2003

(87) PCT Pub. No.: WO02/071946

PCT Pub. Date: Sep. 18, 2002

(65) Prior Publication Data

US 2004/0086076 A1 May 6, 2004

(30) Foreign Application Priority Data

Mar. 9, 2001 (JP) .............................. 2001-067150

(51) Int. Cl.
*G01N 23/00* (2006.01)

(52) U.S. Cl. .......................................... 378/16; 378/4

(58) Field of Classification Search ............... 378/4–20
See application file for complete search history.

(56) References Cited

U.S. PATENT DOCUMENTS

| 4,624,007 A | * | 11/1986 | Muranushi ..................... 378/4 |
| 4,649,555 A | * | 3/1987 | Matsubayashi ................ 378/4 |
| RE35,848 E | * | 7/1998 | Tanaka ........................ 378/16 |
| 6,307,912 B1 | * | 10/2001 | He et al. ..................... 378/19 |
| 6,424,692 B1 | * | 7/2002 | Suzuki ......................... 378/4 |

* cited by examiner

*Primary Examiner*—Craig E. Church
(74) *Attorney, Agent, or Firm*—Antonelli, Terry, Stout and Kraus, LLP.

(57) ABSTRACT

In an X-ray CT device, the scan conditions of the device are set, a three-dimensional X-ray passage length model of the body being examined is generated from a scanogram image of the body, the control pattern of the tube current is automatically set on the basis of the scan conditions and the three-dimensional passage length model, and the dose which will be given will be calculated and displayed on the basis of the control pattern of the tube current, and three-dimensional CT value model data of the body generated on the basis of a standard human body. The scanogram image of the body and the control pattern of the tube current are displayed next to each other or overlap to allow an operator to edit the control pattern while viewing the body, so that a suitable tube current can be set.

14 Claims, 12 Drawing Sheets

DISPLAY EXAMPLE

X-RAY CT DEVICE AND IMAGE DISPLAYING METHOD THEREFOR

TECHNICAL FIELD

The present invention relates to an X-ray CT device which controls the exposure of X-rays applied to an object to be examined by controlling the electric current (tube current) supplied to an X-ray source (X-ray tube) during scanning and, more particularly, the invention relates to a technique which makes it possible to set the curve of a change in the tube current during the scanning in consideration of the dose of X-rays given to the object and the image quality.

BACKGROUND OF THE INVENTION

In a conventional X-ray CT device, the scan conditions, including the tube voltage and the tube current supplied to the X-ray tube, are kept constant while scanning the same cross-section.

Further, a helical scan for taking a photograph by scanning the body being examined along a spiral path has been widely used in recent years, but the conditions of scanning in the body axis direction are maintained constant during such a scan.

Accordingly, for example, when the cross-section of the body to be examined is not a concentric circle, but is elliptical with respect to the rotating axis of a CT scanner (also called a scanner), the length of the path through the body where the X-ray passes is greatly changed in accordance with the rotating angle of the X-ray source. Therefore, a problem exists in that the amount of transmitted X-rays may be excessive or insufficient while scanning one cross-section.

Further, the X-ray absorption coefficient is greatly different in the internal organs of low density in the chest, such as the lungs, etc., and the internal organs of high density in the abdomen such as the liver, etc. Therefore, a the scan is continuously performed from the chest to the abdomen and an X-ray amount suitable for the lungs is set, the X-ray amount will be insufficient for the liver. In contrast to this, when an X-ray amount suitable for the liver is set, the X-ray amount will be excessive in the lungs.

When the transmitted X-ray amount is insufficient, the S/N (SN ratio) becomes worse because of the reduced amount of X-ray photons detected by the X-ray detector (hereinafter abbreviated as a detector), and the S/N of the entire cross-sectioned image obtained by image reconstruction becomes worse as a result. Conversely, when the transmitted X-ray amount is too large, unnecessary X-rays are applied to the body being examined.

A method for controlling the tube voltage, as disclosed in JP-A-53-110495, and methods for controlling the tube voltage, as disclosed in JP-A-9-108209 and JP-A-10-309271, have been proposed for solving these problems.

However, the method for controlling the tube voltage as described in JP-A-53-110495 has a problem in that, during the scan, the spectrum of the X-rays is changed, since the tube voltage is changed, and thus the CT value cannot be determined. Therefore, a method for controlling the tube current is the main method used at present.

As a method for optimally controlling the tube current in accordance with the characteristics of the body being examined, there is a method of controlling the tube current based on data indicating the amount of X-rays that have passed through the object in the first half period of the scanner rotation, as described in JP-A-10-309271, and a method of determining a pattern for controlling the tube current in advance in accordance with the position of the body which is being examined on the basis of scanograms scanned from two different directions, as described in JP-A-9-108209.

However, the method using the data of X-ray passage through the object in the first half of the scanner rotation, as described in JP-A-10-309271, has a problem in that the X-ray data deviates from one cross-section to another, particularly in a helical scan with a large scan pitch. Further, this method cannot cope with an area in which the X-ray absorption characteristics of the body being examined vary greatly e.g. above and below the diaphragm.

In the method for obtaining the scanograms from two different directions, as described in JP-A-9-108209, the unnecessary X-ray exposure to the body being examined is increased by taking the scanogram photograph twice. Accordingly, this method is contrary to its purpose, i.e. reduction of the exposure through tube current control.

The inventors of the present invention have also proposed a method of optimally controlling the tube current in accordance with characteristics of the body being examined, as described in JP-A-2001-276040. The method described is JP-A-2001-276040 relates to the use of an X-ray CT device that is capable of realizing low exposure scanning by not sending unnecessary X-rays to the body being examined. In this method, a model representing the length of the body where the X-ray passes for each rotation angle of a scanner is stored in memory in advance. When the body is to be scanned, the tube current producing the X-rays is set for every rotation angle of the scanner based on this model. The scan measurement is then made and a cross-sectional image is reconstructed.

The method described in JP-A-2001-276040 lays emphasis on the generation of the X-ray passage length model of the body being examined and the setting of the tube current based on the length of the X-ray passage through the body as given by this X-ray passage length model. However, there is no consideration of the actual amount of X-rays being applied to the body by this set tube current or the X-rays received by the internal organs within the body.

In consideration of the above-mentioned problems, an object of the present invention is to provide an X-ray CT device and a data processing method which make it possible to calculate the exposure, inside and outside the body being examined, to tube current controlled according to a variation control pattern that is automatically set, based on the X-ray passage length model of the body being examined, and to allow an operator to reset the variation control pattern of the tube current in consideration of the X-ray exposure of this body being examined.

SUMMARY OF THE INVENTION

To achieve the above-stated object, an X-ray CT device of the present invention comprises an X-ray source for sending X-rays to a body to be examined, a high voltage generator for supplying a high voltage electric current to the X-ray source, an X-ray detector arranged on the side of the body to be examined at a position opposite from the X-ray source for detecting the amount of X-rays passing through the body being examined, scan condition setting means for setting the conditions for scanning so as to obtain a cross-sectional image of the body, scanogram image collecting means for obtaining a scanogram image of the body being examined, display means for displaying the obtained scanogram image, scanning position setting means utilizing the displayed scanogram image for setting the position from which the body is scanned to obtain a cross-sectional image, cross-section reconstructing means for sending X-rays from the X-ray source all around the body being examined while rotating the X-ray source according to the set scan conditions including the scanning position and visually reconstructing the cross-section of the body from the amount of X-rays passing through the body as detected by the X-ray detector, and control means for causing the cross-sectional image to be displayed on the display means.

The X-ray CT device further comprises passage length calculating means for calculating the length of the passage of X-rays through the body on the basis of the scanogram image, and electric current setting means for setting a high voltage generator to generate an electric current to be supplied to the X-ray source in order to produce the X-rays to be sent to the part of the body being examined based on the calculated X-ray passage length and the scan conditions.

In the above-described construction, the X-ray CT device comprises passage length calculating means for calculating the length of the passage of X-rays through the body being examined on the basis of the scanogram image, and the electric current setting means for setting in the high voltage generator an electric current value for generating the X-rays in the X-ray source, this value corresponding to the part of the body being examined from the calculated X-ray passage length and the scan condition. Accordingly, resetting of the tube current curve and control of the tube current can be automatized.

Further, the above-described passage length calculating means may calculate the X-ray passage length by using data of the X-ray amount sent to the body being examined and the standard human body model data.

Further, the above-described electric current value setting means may set the high voltage generator at a first electric current value calculated from the scan conditions, or it may set the high voltage generator at the maximum value and the minimum value of a second electric current value according to the X-ray passage length of the part of the body being examined. Further, the above-described electric current value setting means may calculate a first electric current value from the scan conditions, and it may also calculate a second electric current value according to the part of the body being examined from this first electric current value and the X-ray passage length, and it may set the high voltage generator at this second electric current value. Further, the above-described electric current value setting means may set the high voltage generator at an electric current value based on the gamma value of the characteristic curve of the electric current value supplied to the X-ray source and the X-ray passage length of the part of the body being examined.

Further, the above-described control means may display the electric current value curve set according to the part of the body being examined and the scanogram image of the body being examined in parallel with each other, or it may overlap the variation control pattern and the scanogram image in the display.

The present invention further comprises an X-ray CT device comprising an X-ray source for sending X-rays to a body being examined, a high voltage generator for supplying a high voltage electric current to the X-ray source, an X-ray detector arranged opposite to the X-ray source with respect to the body being examined and which detects amounts of X-rays passing through the body being examined, scan condition setting means for setting scan conditions for obtaining a cross-sectional image of the body, scanogram image collecting means for obtaining a scanogram image of the body being examined, display means for displaying the obtained scanogram image, scan position setting means for setting on the displayed scanogram image the position of scanning to obtain the desired cross-sectional image of the body, condition setting means for setting the scan condition of a CT scanner, cross-sectional image reconstructing means for irradiating the circumference of the body being examined including the set scanning position with X-rays from the X-ray source while rotating the X-ray source and reconstructing the cross-sectional image from the X-ray passage data of the body being examined as detected by the X-ray detector, and control means for causing the reconstructed cross-sectional image to be displayed on the display means; wherein the X-ray CT device further comprises passage length calculating means for calculating the length of the passage of X-rays through the body being examined on the basis of the scanogram image, and dose calculating means for calculating the X-ray dose corresponding to the electric current value for generating the X-rays based on the calculated X-ray passage length of the part of the body being scanned and the scan conditions, and the control means displays the calculated dose next to the scanogram image, or else overlaps the calculated dose and the scanogram image in the display.

In accordance with this construction, the dose given to the body being examined during the scan is calculated by the dose calculating means and is displayed on the display means. Accordingly, an operator can evaluate the exposure of X-rays to the body being examined. Further, the control pattern of the tube current can be reset according to an evaluation of the X-ray exposure results.

The present invention also comprises an X-ray CT device with an X-ray source for sending X-rays to a body being examined, a high voltage generator for supplying a high voltage electric current to the X-ray source, an X-ray detector arranged opposite to the X-ray source relative to the body being examined and which detects the amount of X-rays passing through the body being examined, scan condition setting means for setting scan conditions for obtaining a cross-sectional image of the body, scanogram image collecting means for obtaining a scanogram image of the body being examined, display means for displaying the obtained scanogram image, scan position setting means for setting on the displayed scanogram image the position of scanning to obtain the desired cross-sectional image of the body, condition setting means for setting the scan conditions of a CT scanner, cross-sectional image reconstructing means for transmitting X-rays from the X-ray source while rotating the X-ray source around the body being examined at the set scan position and which reconstructs the cross-sectional image from the X-ray passage data of the body being examined as detected by the X-ray detector, and control means for causing the reconstructed cross-sectional image to be displayed on the display means; wherein the X-ray CT device further comprises passage length calculating means for calculating the length of the passage of X-rays through the body being examined on the basis of the scanogram image, and dose distribution calculating means for calculating the distribution within the body being examined of doses of X-rays generated according to an electric current value calculated from the calculated X-ray passage length of the part of the body to be scanned and the scan conditions, and the control means displays the calculated dose distribution next to the scanogram image, or overlaps the calculated dose distribution and the scanogram image in the display.

In accordance with this construction, the integrated amount of the X-rays which have irradiated the body over a period of time calculated by the above-described dose calculating means is sequentially displayed as a dose distribution on the display means during the scan. With this construction, since the integrated amount of X-rays irradiating the body being examined is sequentially displayed during the scan, the operator can easily determine the details of the X-ray exposure amount to the body being examined during the scan.

The present invention also comprises a method including a step of obtaining a scanogram image for obtaining a cross-sectional image of a body being examined and displaying this scanogram image in a display device, a step of displaying a variation control pattern of a first supply electric current to an X-ray source corresponding to the displayed scanogram image, a step of editing the variation control pattern of the first supply electric current into a variation control pattern of a second supply electric current by operating means based on this scanogram image, and a step of obtaining the cross-sectional image of the body being examined on the basis of the edited variation control pattern of the second supply electric current and displaying this cross-sectional image on display means.

In accordance with this method, the variation control pattern of the tube current is arranged in parallel with the scanogram image of the body being examined, or it is superposed on the scanogram image of the body being examined on the screen of the display means. Accordingly, while the operator, for example, views the part of the body to be scanned, the operator can edit the variation control pattern of the tube current. Accordingly, a tube current suitable for that part can be easily set.

Further, in the X-ray CT device of the present invention, the above-described tube current setting means sets the variation control pattern of the tube current so that the maximum value and the minimum value of the tube current, representing two of the scan conditions, correspond to the maximum value and the minimum value of the X-ray passage length through the three-dimensional model of the body, where a larger value of the tube current corresponds to a larger X-ray passage length through the model. In this construction, the magnitude of the tube current proportional to the X-ray amount sent by the X-ray source is set proportionately to the length of the passage of X-rays through the body being examined. Accordingly, the dose given to the body being examined corresponds to the length of the passage of X-rays through the body being examined, and both the dose received by the body and the dose passing through the body are kept at a standard level. This contributes to an improvement of the quality of the CT image and a reduction in the X-rays received by the body being examined.

In the X-ray CT device of the present invention, the variation control pattern of the tube current is further set so that, at an arbitrary X-ray source position, a proportional relation between the difference of the X-ray passage length of the model from the minimum value of tube current and the difference of the set value of the tube current from the minimum value of tube current is maintained. With this construction, there is a functional relation between the X-ray passage length model data and the variation control pattern of the tube current determined by the value of $\gamma$. Accordingly, the variation control pattern of the tube current can be automatically set merely by setting the maximum value and the minimum value of the tube current and the value of $\gamma$. Therefore, the variation control pattern of the tube current can be very easily set.

Further, in the X-ray CT device of the present invention, the above-described scanogram analyzing means makes elliptical models (two-dimensional X-ray passage length models) of the X-ray passage lengths of plural cross sections of the body being examined on the basis of the scanogram images in the front face direction or the side face direction of the body being examined, and it generates a three-dimensional X-ray passage length model of the body being examined by arranging the plural elliptical models in the body axis direction. With this construction, the X-ray exposure to the body being examined can be reduced, since the three-dimensional X-ray passage length model of the body being examined can be generated by one scan for the scanogram.

In the X-ray CT device of the present invention, in the above-described elliptical model of the length of the passage of X-rays through the cross section of the body being examined, the length of the X-ray passage with the maximum X-ray attenuation is set to be the minor axis or the major axis in the corresponding section of the scanogram. This elliptical model is modeled by an elliptical shape in which an integrated value obtained by integrating the X-ray passage length corresponding to the X-ray attenuation over the entire section in the direction perpendicular to the X-ray passage length direction in the above-mentioned section is set to be the area. With this construction, the elliptical model of the X-ray passage length can be easily obtained from measured data of the scanogram image of the body being examined.

Further, the X-ray CT device of the present invention has dose distribution calculating means for calculating the dose distribution within the body being examined on the basis of the variation control pattern of the tube current and the three-dimensional CT value model of the body being examined, as calculated in advance, and displaying the calculation results. With this construction, the operator can determine the dose distribution within the body due to the CT scanning in advance by use of the dose distribution calculating means, and can judge whether the scan can be executed or not in consideration of the degree of X-ray exposure of the internal organ being diagnosed.

In the X-ray CT device of the present invention, the above-described dose distribution calculating means further calculates the dose distribution within the body being examined on the basis of the amount of X-rays sent to the body, the variation control pattern of the tube current, and three-dimensional $\mu$ (linear attenuation coefficient) value model data of the body being examined as calculated from the three-dimensional CT value model of the body being examined.

In the X-ray CT device of the present invention, the dose distribution calculating means further displays a graph of the dose distribution within the body being examined overlapped with the part of the body being scanned on the screen of the display means. Further, isodose lines of the dose are displayed, comprising a graph of the dose distribution within the body being examined. With this construction, the image of the part of the body being scanned and the graph of the dose distribution within the body are overlapped on the display screen. Accordingly, the dose of the internal organ being diagnosed can be determined at a glance, and it is possible to easily judge whether the X-ray exposure is excessive or insufficient.

The X-ray CT device of the present invention further has means for generating a CT value model of the body being examined for generating the three-dimensional CT value model data of the body being examined on the basis of the standard human body CT value model data generated by CT-scanning a standard human body phantom, and the scanogram image data of the body being examined. In this construction, since the body CT value model generating means for generating the three-dimensional CT value model of the body being examined from the scanogram image of the body being examined is provided, the body CT value model can be generated merely by obtaining scanogram image data of one preliminary scan of the body being examined which had not been CT scanned previously.

In the X-ray CT device of the present invention, the above-described means for generating a CT value model of the body being examined further generates the three-dimensional CT value model of the body being examined from the CT images obtained by the past CT scanning of the body being examined. With this construction, since the three-dimensional CT value model data of the body being examined is obtained from the past CT image of the body being examined, the time for generating the body CT value model can be shortened by effectively utilizing the past CT images.

BEST MODE FOR CARRYING OUT THE INVENTION

Various embodiments of the present invention will be explained with reference to the accompanying drawings.

Figure 1:
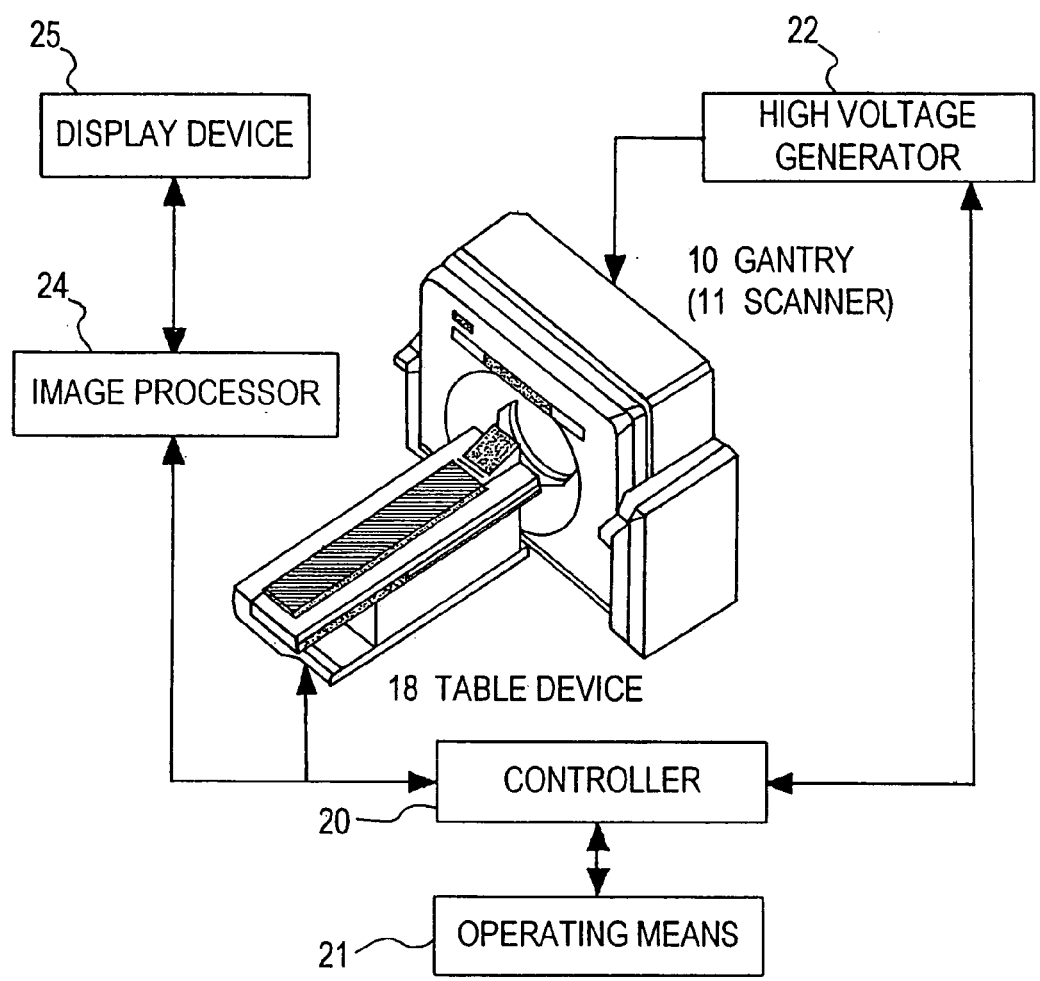
FIG. 1 is a block diagram showing the overall construction of an X-ray CT device in accordance with the present invention.

FIG. 1 is a block diagram showing the overall construction of an X-ray CT device in accordance with the present invention. As shown in FIG. 1, this X-ray CT device is mainly constructed by a gantry 10 mounting an X-ray source 12, a detector 13, etc., and having a built-in scanner 11 that is able to be continuously rotated around a body 15 being examined, a controller 20 for overall control of the device, a high voltage generator 22 for supplying a high voltage to the X-ray source 12, an image processor 24 for performing preprocessing and reconstruction of image data or other various kinds of analysis, a display device 25 for displaying an image, a bed (table device) 18 upon which the body 15 being examined is placed, and an operating means 21 for use by an operator to input scan conditions, etc. It is sufficient to rotate the scanner 11 and the body 15 being examined relative to each other. Accordingly, the body 15 being examined may be held still and the scanner 11 may be rotated, or else the scanner 11 may be held still and the body 15 being examined may be rotated.

Figure 2:
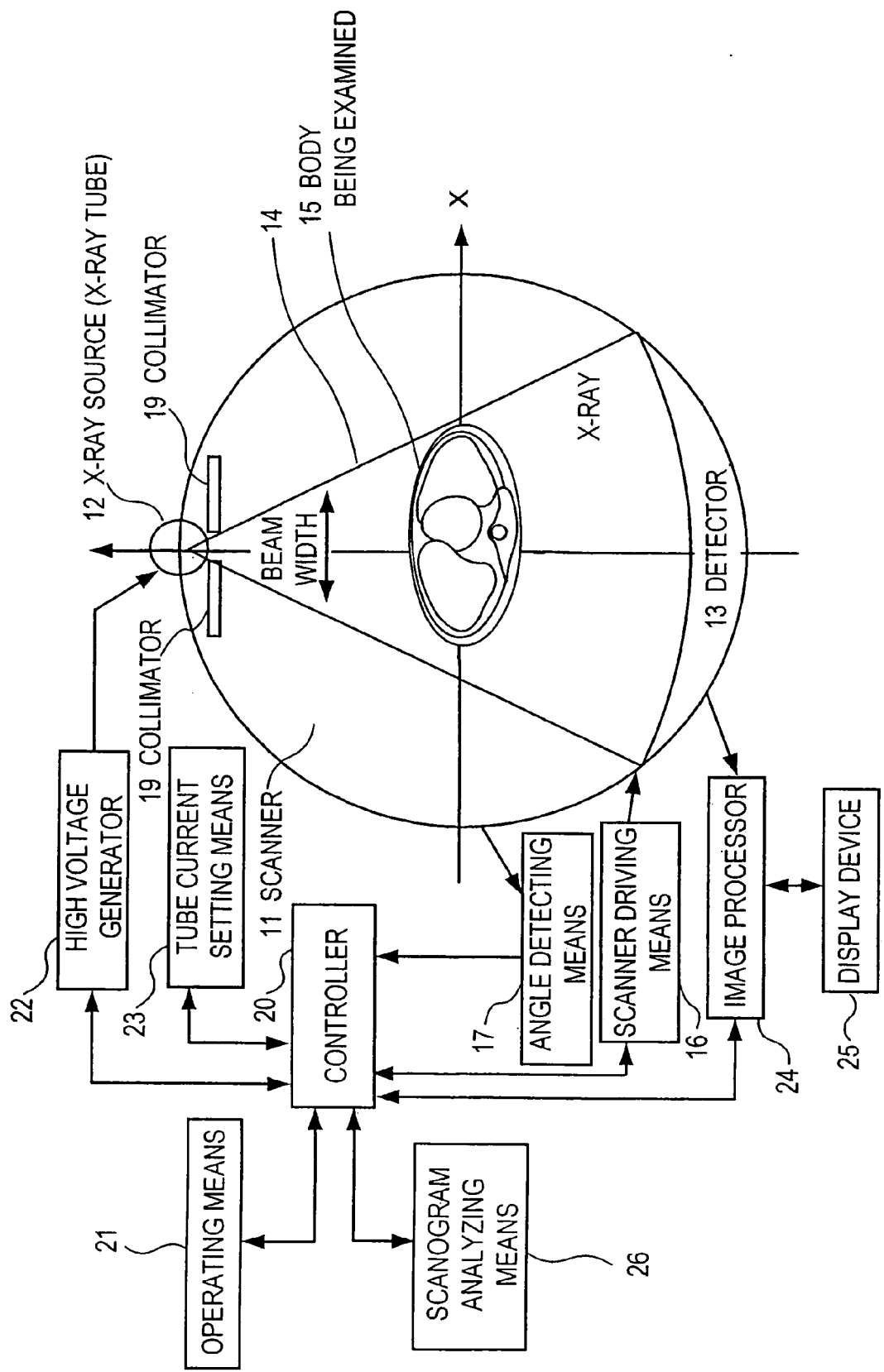
FIG. 2 is a block diagram which shows the structural elements of the main portion of the X-ray CT device in accordance with the present invention.

FIG. 2 shows the structural elements of a main portion of the X-ray CT device in accordance with the present invention. The details of the scanner 11 will first be explained with reference to FIG. 2. In FIG. 2, the X-ray source 12 and the detector 13 are arranged at positions opposed by 180 degrees in the scanner 11. An X-ray beam 14 emitted from this X-ray source 12 is changed to an X-ray beam having a fan shape limited in width and thickness by a collimator 19, and this beam is transmitted to the body 15 being examined. The X-ray source 12 is controlled by the controller 20 through the high voltage generator 22. The scanner 11 detects the rotation angle by use of scanner angle detecting means 17, and then the controller 20 controls the operation of a scanner driving means 16 on the basis of this detected rotation angle, and the scanner driving means 16 operates the scanner 11. The detector 13 detects the X-ray beam 14 transmitted through the body 15 being examined, and detected data is collected as scan data showing the attenuation of the X-rays due to their passage through the body 15 being examined. The scan data are correlated with the scanner angle and other data stored in the controller 20 in the image processor 24, and the result is displayed as a cross-sectional image on the display device 25 after the processing of image reconstruction, etc. is performed.

The structural elements of the main portion, other than the scanner 11, in accordance with the present invention will be explained next. In FIG. 2, the scanner 11 is indirectly connected to the controller 20 for overall control of the entire device through the scanner driving means 16. The X-ray source 12 is indirectly connected to the controller 20 through the high voltage generator 23. The detector 13 is indirectly connected to the controller 20 through the image processor 24. The operating means 21, a tube current setting means 22, the image processor 24 and a scanogram analyzing means 26 are directly connected to the controller 20. The controller 20 controls the X-ray irradiation to the body 15 using the connection between the scanner 11, X-ray source 12, and the detector 13, and it controls the collection of scan data (detecting data) by the detector 13. The image processor 24 sequentially reconstructs cross-section images on the basis of the collected scan data in accordance with commands of the controller 20.

In the X-ray CT device in accordance with the present invention, various kinds of preparations for setting the scan conditions are performed before a main scan is performed for obtaining a cross-sectional image of the body being examined. Among these preparations, the scanning of a scanogram image for determining the position of the body being examined, the analysis of scanogram image data for setting the tube current, the determination of a variation control pattern of the tube current for the scan, etc. are performed through the controller 20.

The main structural elements involved in these preparations include the controller 20, the operating means 21, the scanogram analyzing means 26, the tube current setting means 23, the X-ray source 12, and the detector 13. In this preparing operation, the operating means 21 first mainly inputs the scan conditions, such as setting values (maximum value, minimum value) of the tube current, etc. The X-ray source 12 and the detector 13 take a scanogram image without rotating the scanner 11, and this image data is stored in the controller 20. The scanogram analyzing means 26 analyzes the scanogram image data, and the length of the passage of X-rays through the body at each cross-sectional position in the body axis direction, and every rotation angle of the scanner is used to model three-dimensional shape data as accurately as can be calculated. The data of this model (hereinafter called a three-dimensional X-ray passage length model of the body being examined) is stored in the controller 20. The tube current setting means 23 automatically determines a series of tube current values changing with the passage of time in accordance with a change in the X-ray passage length of the part of the body being scanned. This series is the variation control pattern of the tube current determined on the basis of the tube current setting value inputted from the operating means 21 and the data of the three-dimensional X-ray passage length model of the body being examined. The variation control pattern of the tube current determined in this way is stored in the controller 20, and it is sequentially called out in accordance with the part of the body being scanned at the main scan time, and the tube current of the X-ray source 12 is changed.

In accordance with the present invention, the amount of X-rays irradiating the body 15 is calculated in advance before the main scan on the basis of the variation control pattern of the tube current determined above. In the operation of X-ray devices, the mAs value is normally used as an amount corresponding to the X-ray irradiation, and the mAs value is also adopted in this calculation. This mAs value is a product of the tube current (mA) and irradiation time (s), and it is proportional to the sum total of the amount of X-rays transmitted from the X-ray source 12 when the tube voltage is constant (the tube voltage is constant in the X-ray CT device in many cases). Therefore, the mAs value is used as a reference of the X-ray amount. The calculated amount of X-rays irradiating the body 15 is evaluated by an operator as the estimated exposure dose to the body being examined.

Figure 3A:
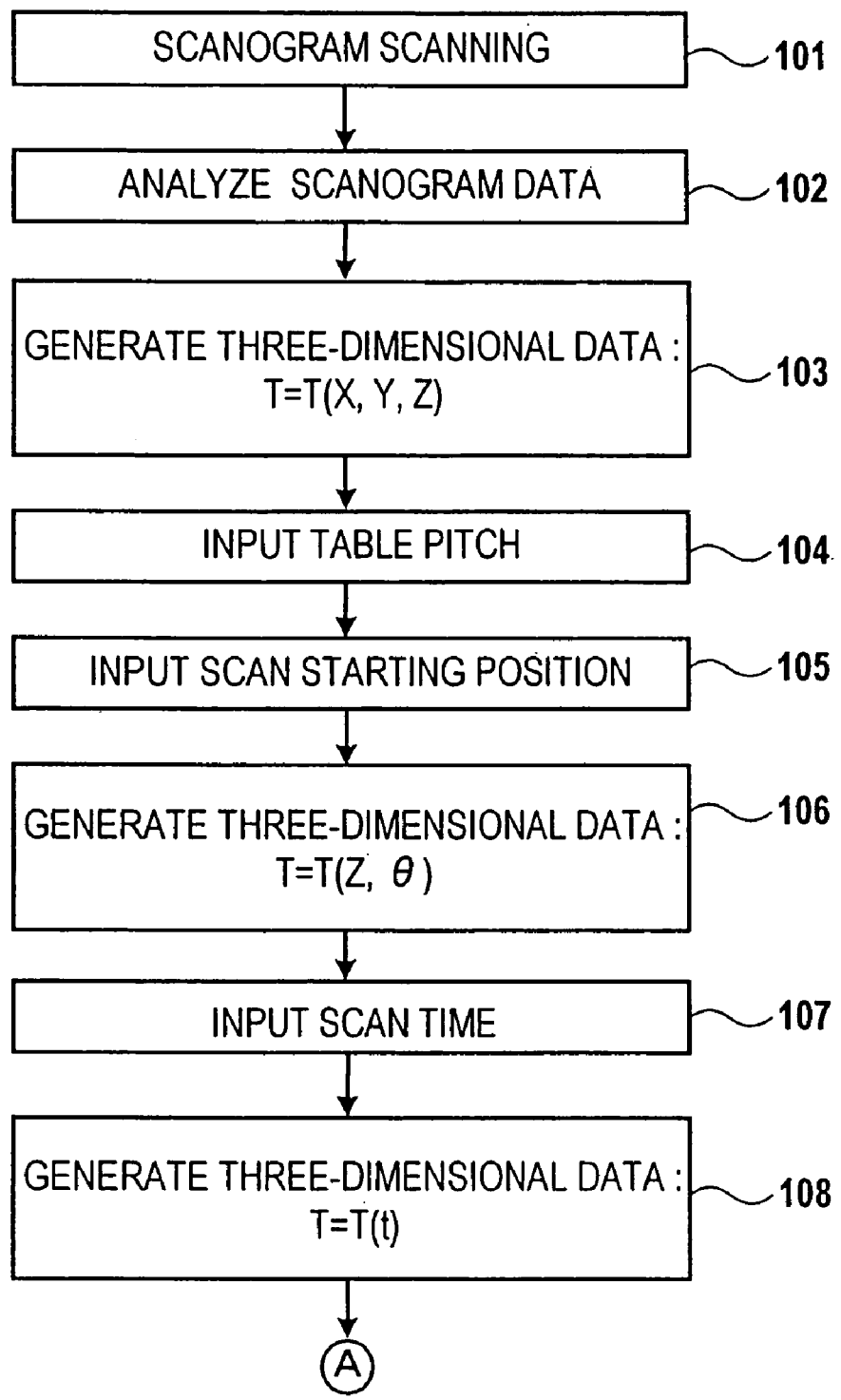
FIGS. 3a and 3b, when combined, comprise a flow chart of the series of operations in a first example of scanning using the X-ray CT device in accordance with the present invention.
Figure 3B:
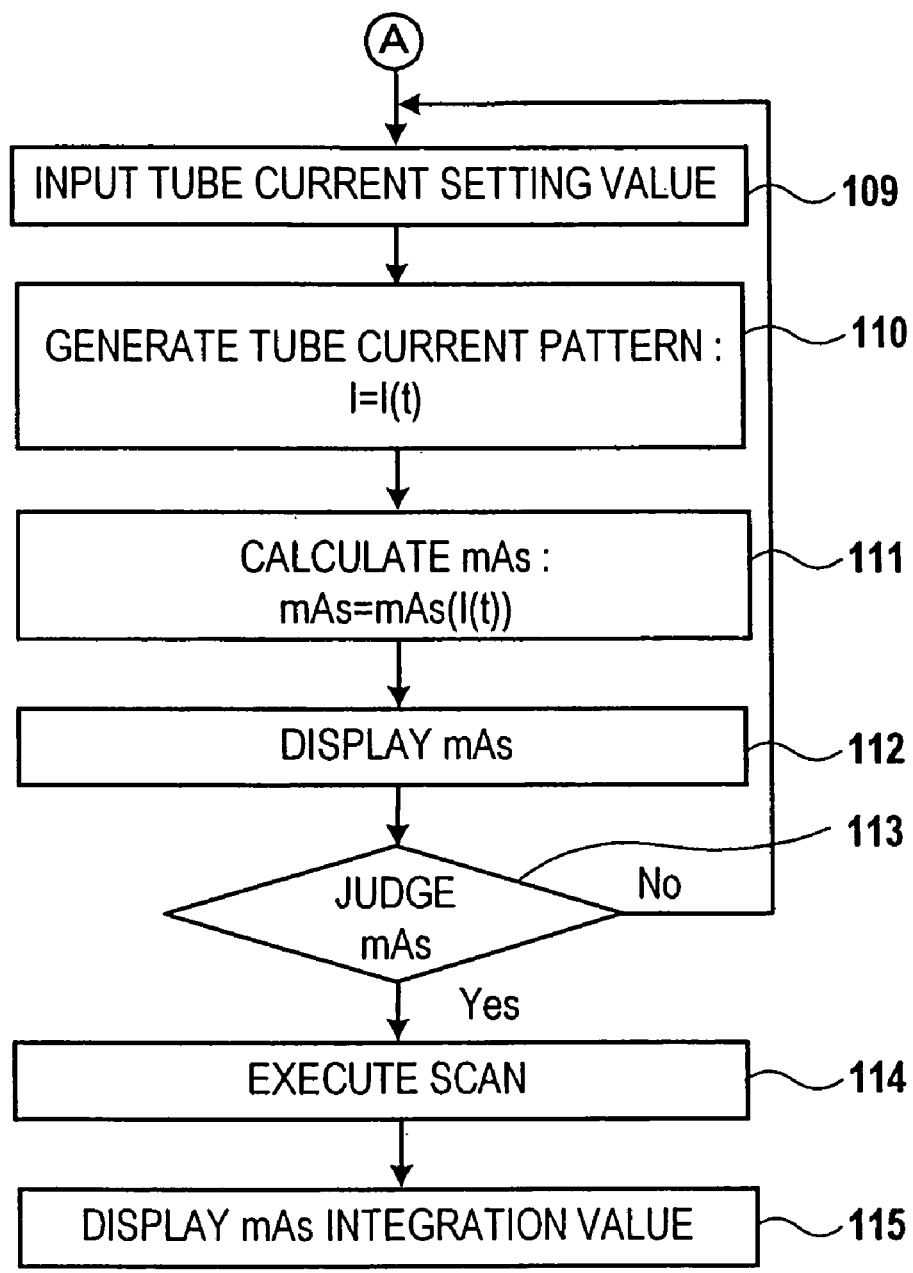

FIGS. 3a and 3b comprise a flow chart of a series of operations of a first scan operation using the X-ray CT device in accordance with the present invention. This scan operation is distinctive for its three-dimensional data generation in steps 103, 106, 108, its tube current pattern generation in step 110, its mAs calculation of a step 111, and its mAs display in step 114. The details of the first scan operation of FIGS. 3a and 3b will be explained next with reference to FIG. 2.

In FIG. 3a, first, a scanogram image of the body 15 is taken in the scanogram scan of step 101. The taking of the scanogram image of the body 15 being examined and the taking of a cross-sectional image are basically the same. In this step, the scanogram image data are obtained by transmitting an X-ray 14 to the front face of the body 15 and collecting detection data in the detector 13 without rotating the scanner 11. The scanogram image obtained at this time is an image in the front face direction. This scanogram image data is sent from the detector 13 to the controller 20, and it is utilized to position the body 15 at the main scan time, and, more particularly, to determine the control pattern for variation of the tube current for controlling the tube current in accordance with the present invention.

Next, in the scanogram data analysis of step 102 and the first three-dimensional data generation of step 103, the scanogram image data is analyzed by the scanogram analyzing means 26 connected to the controller 20, and a three-dimensional X-ray passage length model of the body 15 is generated. In the case where the body 15 is CT-scanned, the three-dimensional X-ray passage length model is a model showing the X-ray passage lengths in their positional relations in the body 15. A method for producing the three-dimensional X-ray passage length model of the body 15 is also disclosed in JP-A-2001-276040.

Figure 4:
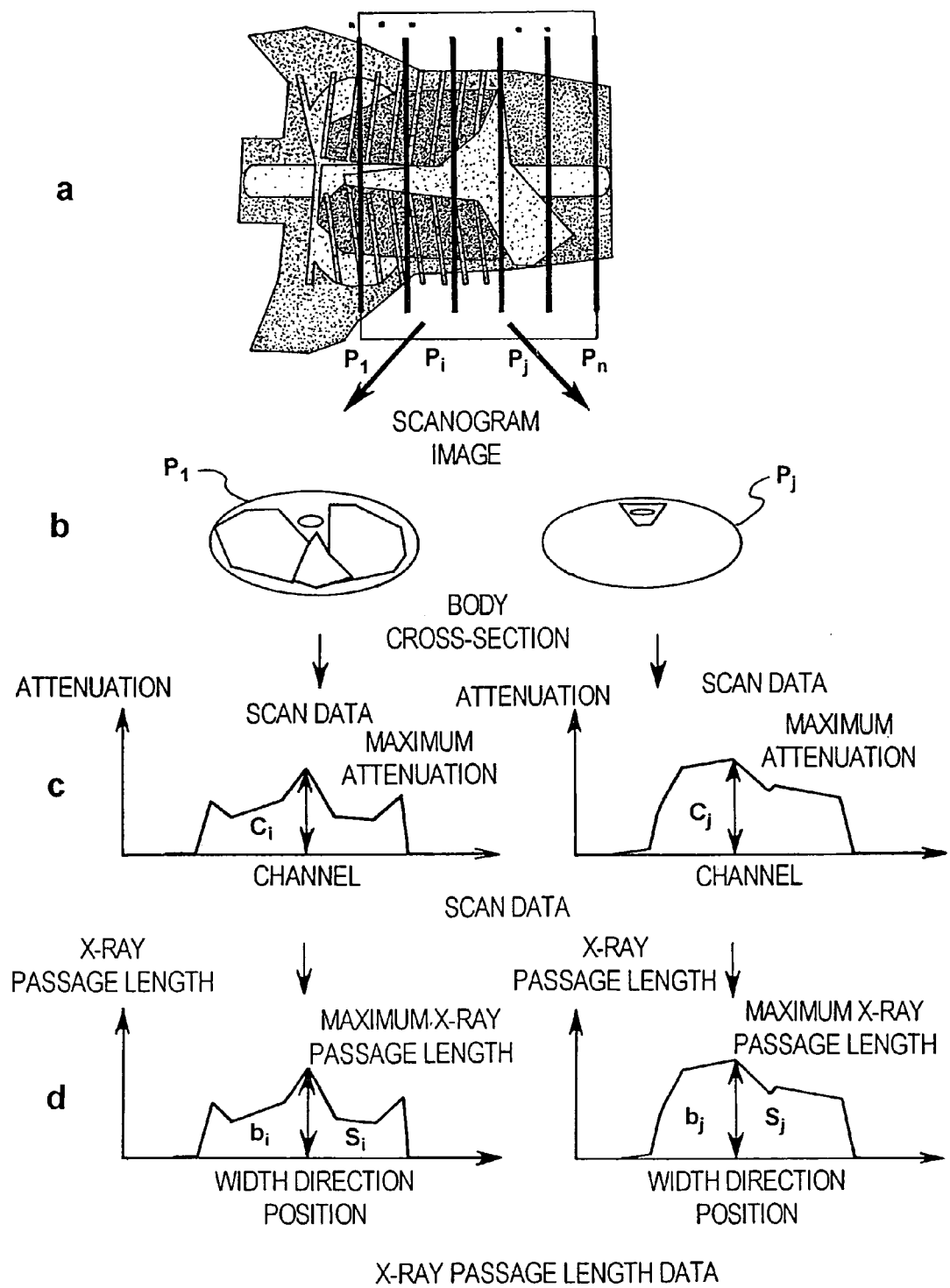
FIG. 4a is a diagram of a scanogram image.
FIG. 4b is a diagram of body cross-section and FIGS. 4c and 4d are graphs showing the correspondence of a scanogram image, slice position and scan data examples.
Figure 5:
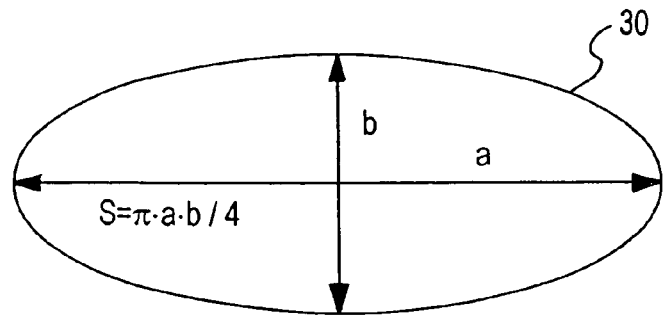
FIG. 5 is a diagram showing a three-dimensional X-ray passage length model in one slice position.

One example of the method for producing the three-dimensional X-ray passage length model of the body 15 will be explained next. FIGS. 4a through 4d are diagrams showing the correspondence of the scanogram image, the slice position and a scan data example. FIG. 5 is a diagram showing the three-dimensional X-ray passage length model in one slice position. FIG. 4a shows the scanogram image 29 of the body being examined, which is scanned in step 101. In the scanogram image 29, an area from the chest to an intermediate position of the abdomen is set as the scanning area. The slice position is selected from such a scanning area of the scanogram image. In the illustrated case, n-slice positions are selected. In FIG. 4a, reference numerals $P_1, ---, P_i, ---, P_j, ---, P_n$ designate slice positions.

FIGS. 4b, 4c and 4d are views illustrating the manner of determination of the three-dimensional X-ray passage length model. If CT cross-sectional images in two arbitrary slice positions $P_i$, $P_j$ are formed, as shown in FIG. 4b, the X-ray attenuation in the longitudinal direction (vertical direction in FIG. 4b) ought to be as shown in FIG. 4c. Since the cross section of a trunk portion of the human body is normally close to an elliptical shape, it is judged that there is no large error when the CT cross-sectional images of the arbitrary slice positions $P_i$, $P_j$ are assumed to be as shown in FIG. 4b. Therefore, the scan data of FIG. 4c is converted to X-ray passage length data, and this data is then integrated to obtain the area along the abscissa. At this time, in the conversion of the scan data of the X-ray attenuation to the X-ray passage length, the data conversion is performed under the consideration that the human body is similar to water for the sake of brevity. When the X-ray attenuation is c and the X-ray passage length is b and the linear attenuation coefficient of water is $\mu_w$, the relation of these amounts is represented by $b = \log c / \mu_w$. With respect to the abscissa, the conversion is performed such that the range of obtained X-ray attenuation data is displayed to be of the same length as the scanned length of the human body. FIG. 4d is a diagram showing distribution of the X-ray passage length data of the body 15 in the slice positions $P_i$, $P_j$ converted from the scan data of FIG. 4c. Maximum X-ray passage lengths in the slice positions $P_i$, $P_j$ in FIG. 4d are $b_i$, $b_j$, and the areas are $S_i$, $S_j$. When the maximum X-ray passage lengths $b_i$, $b_j$ and the areas $S_i$, $S_j$ are considered with respect to the X-ray passage length data of FIG. 4d, it is clear that $b_i$ and $S_i$ are values reflecting the X-ray transmitting situation of the cross-sectional image in the slice position $P_i$, and $b_j$ and $S_j$ are values reflecting the X-ray transmitting situation of the cross-sectional image in the slice position $P_j$.

Therefore, the cross-section in each slice position is modeled by an elliptical shape 30, as shown in FIG. 5, in the three-dimensional X-ray passage length model of the body being examined. In this modeling, the areas of elliptical models $30_i$, $30_j$ in the slice positions $P_i$, $P_j$ are $S_i$, $S_j$, and the minor axes are $b_i$, $b_j$. As a result, where the major axes of the elliptical models $30_i$, $30_j$ are $a_i$, $a_j$, the areas of the elliptical models $30_i$, $30_j$ are represented by the following formulas (1).

$$Si=(\pi \cdot ai \cdot bi)/4$$

$$Sj=(\pi \cdot aj \cdot bj)/4 \quad (1)$$

Accordingly, the major axes $a_i$, $a_j$ are calculated by the following formulas (2).

$$ai=4Si/(\pi \cdot bi)$$

$$aj=4Sj/(\pi \cdot bj) \quad (2)$$

The elliptical X-ray passage length model 30 corresponding to the cross-section image in each slice position is calculated using the foregoing formulas. Accordingly, the three-dimensional X-ray passage length model 30 can be obtained by arranging these elliptical models 30 in the body axis direction. When the pitch of the slice position in the body axis direction is wide, one or more intermediate elliptical models are calculated by interpolation by e.g., the least squares method, between adjacent elliptical models. X-ray passage length data T=T(X,Y,Z) of the body 15 in a three-dimensional coordinates (X,Y,Z) system is generated as data of the three-dimensional X-ray passage length model 30 of the body 15 by the above procedure.

Next, in processes from step 104 to step 110, the variation control pattern of the tube current applied to the X-ray source 12 is set by using the three-dimensional X-ray passage length model 30. First, however, the method of calculating the tube current using the three-dimensional X-ray passage length model 30 will be explained. The three-dimensional X-ray passage length model 30 calculated as described with reference to FIGS. 4a to 4d and 5, shows the length of the passage of X-rays through the cross-section in each slice position of the body being examined. The data of the three-dimensional X-ray passage length model 30 is temporarily stored in a memory including a register of the controller 20. Accordingly, when the scan conditions such as scanning range and table pitch are determined, the data of the model in this scanning range is taken out of the memory, and it is used to generate second and third three-dimensional data and to determine the variation control pattern of the tube current.

Figure 6:
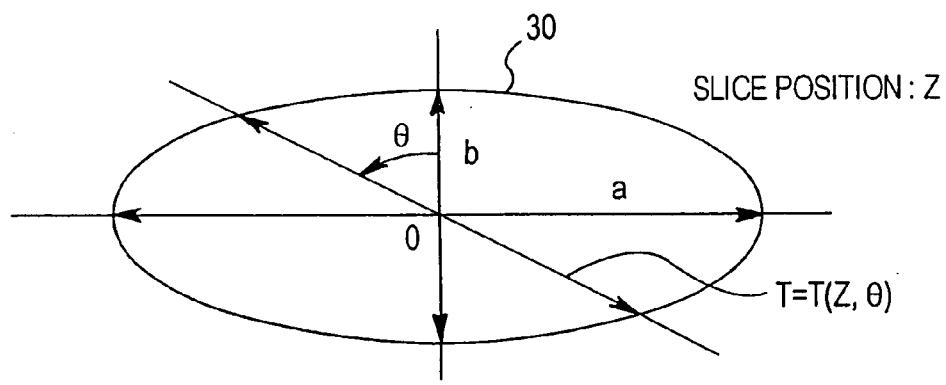
FIG. 6 is a diagram which shows the X-ray passage length model in a slice position Z.

The tube current is determined by the tube current setting means 23 on the basis of the X-ray passage length obtained from the three-dimensional X-ray passage length model 30 at every scanner rotation angle and in each slice position. FIG. 6 shows the X-ray passage length model 30 in a slice position (position along the body axis direction) Z. The tube current at a certain scanner rotation angle is normally adjusted according to the maximum value of the length of the passage of X-rays through the three-dimensional X-ray passage length model at that scanner rotation angle. The X-ray passage length showing this maximum value is obtained by a path passing through the center 0 of the elliptical model 30 of FIG. 6. Therefore, in setting the tube current, it is sufficient to consider only the length of the passage of X-rays through the path passing through the center 0 of this elliptical model 30 at every scanner rotation angle.

Accordingly, when the slice position in FIG. 6 is set to be Z and the scanner rotation angle is set to θ (the starting point of θ is set to be the minor axis direction of the elliptical model 30), the maximum X-ray passage length T in that position of the scan can be represented by T=T(Z,θ), a function of Z and θ.

This maximum X-ray passage length T(Z,θ) is the length of the path passing through the central position 0 of the elliptical model 30. Accordingly, when the value on the major axis is set to a and the value on the minor axis is set to b and the scanner rotation angle is set to θ, the maximum X-ray passage length T(Z,θ) can be represented as in the following formula (3).

$$T(z,\theta)=(a \cdot b)/\sqrt{a^2\cos^2\theta+b^2\sin^2\theta} \quad (3)$$

Here, a, b correspond to $a_i$, $a_j$ and $b_i$, $b_j$ of the formulas (1) and (2).

One example of the method for setting the tube current will be explained next. First, the maximum value (γ maximum value of the path in all the slice positions $P_1$ to $P_n$) of the path in the entire scanning range of the body being examined is labeled $T_{max}$, and the minimum value (similarly, a minimum value of the path) is labeled $T_{min}$. These values are already known when the three-dimensional X-ray passage length model 30 is made. When the tube current is changed within the range of a maximum value $I_{max}$ (mA) and a minimum value $I_{min}$ (mA), the maximum value and the minimum value of the tube current, respectively, correspond to the maximum value and the minimum value of the path and a linear relation is formed between the tube current and the path, in this example. The relation of the tube current I and the path T is represented as in the following formula (4).

$$I=\{(T-T_{min})(I_{max}-I_{min})\}/(T_{max}-T_{min})+I_{min} \quad (4)$$

Here, since the path T corresponds to T(Z,θ), the tube current I is a linear function of (Z,θ), and it is calculated for every slice position Z and scanner rotation angle θ.

Reference will be made once again to the flow chart of FIG. 3. In the processes of step 104 and step 105, an operator in the process of setting scan conditions inputs a table pitch value and a scan starting position value through the operating means 21, while referring to the scanogram image. The CT scanning range, the slice position and the scan rotation angle of the body being examined are determined by these input data. The coordinate system at this time is preferably the (Z,θ) coordinate system as mentioned above, and the data of the scan condition are also preferably data of the (Z,θ) coordinate system.

Next, in the process of step 106, the data of a second three-dimensional X-ray passage length model are generated. The data generated in this process consists of a maximum X-ray passage length at every slice position Z and scan rotation angle θ, and this data can be calculated using the formula (3) from the data of the first three-dimensional X-ray passage length model. Accordingly, the data of the first three-dimensional X-ray passage length model is read out from the memory of the controller 20, and the calculation is performed. This result is represented in the form T=T(Z,θ).

Next, in the process of step 107, the scan time is inputted using the operating means 21, and this value is stored as one of the scan conditions. When the scan starting position, the table pitch and the scan time are determined, the position (Z,θ) of the X-ray source 12 during the scan can be represented as a function of the time t which has passed after the scan start. Accordingly, the second three-dimensional X-ray passage length model of the body being examined in each scan position, i.e., the maximum X-ray passage length T, also can be represented as a function T=T(t) of the time t. Therefore, in the generation of the third three-dimensional X-ray passage length model in step 108, the function of the maximum X-ray passage length T is converted from T=T(Z,θ) to T=T(t).

Next, referring to FIG. 3b, in the input of a tube current setting value in step 109, the operator inputs the setting values of the tube current, e.g., the maximum value $I_{max}$ and the minimum value $I_{min}$ of the tube current during the scan, using the operating means 21. In the generation of the tube current pattern in step 110, the tube current setting means 23 reads out the data T(t) of the three-dimensional X-ray passage length model from the controller 20 and automatically determines the variation control pattern of the tube current varying according to the part of the body being scanned, on the basis of the tube current setting values. At this time, the value of the tube current during the scan is set to correspond with the X-ray passage length T(t). However, the variation control pattern of the tube current is determined so as to cause the minimum tube current to flow at the time of the minimum X-ray passage length T(t) and to cause the maximum tube current to flow at the time of the maximum X-ray passage length T(t). There are various other functions in addition to the linear function expressed by the formula (4) giving the relation of the X-ray passage length T(t) and the value of the tube current (here, T of the formula (4) corresponds to T(t)).

The tube current is determined as a function of the time t following the three-dimensional X-ray passage length model of the body being examined, as mentioned above. Accordingly, the variation control pattern of the tube current can be represented as I=I(t). The variation control pattern I=I(t) of the tube current determined in this way is stored in the controller 20, and it is read out sequentially in accordance with the part of the body being scanned, the tube current during the scan being controlled through the high voltage generator 22.

Figure 7:
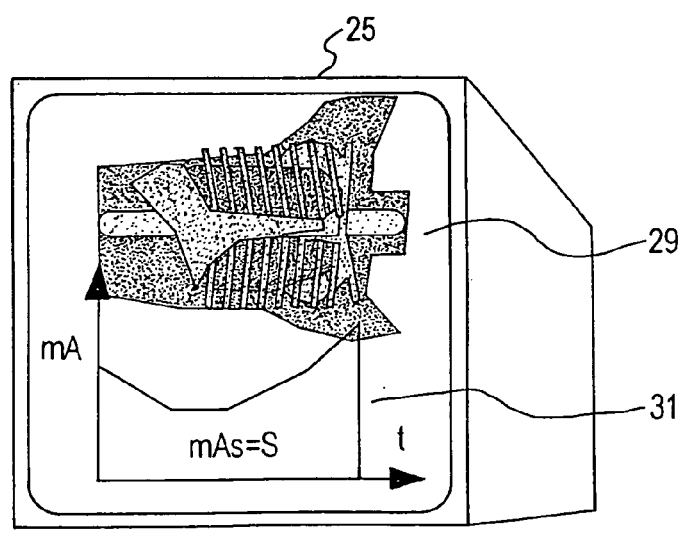
FIG. 7 is a diagram which shows a displayed example of a variation control pattern of the tube current.

FIG. 7 shows an example of the display of a variation control pattern of the tube current (in the following display examples of the variation control pattern of the tube current including this example, the overall periodic change of the tube current with change of the scanner rotation angle θ is omitted and only a change due to the slice position is shown). This is displayed so as to correspond with the scanogram image 29 on the screen of the display device 25. In the variation control pattern 31 of the tube current, the ordinate is the tube current value (mA), and the abscissa is the time t after the scan start. In the case of the display example, the tube current is an intermediate value in an initial period (abdomen) of the scan, and it is a minimum value in a middle period (between the abdomen and the chest), and it is a maximum value in a final period (the chest). Since the tube current value and the part being scanned can be matched with each other at a glance by arranging the variation control pattern 31 of the tube current and the scanogram image 29 in parallel on the same screen, as shown in this display example, it is effective in helping judge the propriety of the tube current value.

Next, in the process of the mAs calculation carried out in step 111, the amount of X-rays irradiating the body 15 during the scan is calculated on the basis of the variation control pattern of the tube current determined in step 110. Here, as mentioned above, mAs as a product of the tube current (mA) and the irradiating time (s) is used as a reference value of the X-ray amount irradiating the body being examined. Accordingly, in this step, the variation control pattern I=I(t) of the tube current is integrated over time, and the X-ray amount mAs irradiated to the body being examined is calculated. This integration is performed by the following formula (5).

$$mAs(t) = \int_0^t I(t')dt' \tag{5}$$

The mAs value calculated here corresponds to the amount of X-rays irradiating the body being examined and is not itself the X-ray amount. Accordingly, it is necessary to find the relation of the X-ray amount and the mAs value accurately by experiment, so that conversion between the X-ray amount and the mAs value can be performed in advance.

Calculation of the amount of X-rays mAs irradiating the body 15 will now be considered, using the variation control pattern 31 of the tube current shown in FIG. 7 as an example. In this case, the variation control pattern 31 of the tube current is I=I(t) and is a function of time. Accordingly, the calculation of mAs by integration of this function involves the calculation of the area under the curve of the variation control pattern 31 of the tube current. Therefore, the area S of the figure of the variation control pattern 31 of the tube current corresponds to mAs.

Next, in the process of display of the mAs calculating value carried out in step 112, the value of mAs calculated in step 111 is displayed on the screen of the display device 25. In step 111, the stage where the variation control pattern of the tube current is generated, the value of mAs corresponding to the amount of X-rays irradiating the body being examined is calculated over the entire area of a scan range of the body being examined. Accordingly, this mAs value is presented to the operator in this step 112 as a standard for the operator to judge whether the scan should be started or not.

In the process of the mAs judgment of step 113, the operator judges the propriety of mAs as a whole. Namely, the operator compares the benefits of the CT scanning to be performed and the harm to the body being examined due to the X-ray exposure, and judges whether the value of mAs as a whole is too large or not. When the operator judges that mAs as a whole is too large, the operator reduces the setting value of the tube current. In this case, the operation is returned to step 109, and the operator again inputs the tube current setting value and resets the variation control pattern of the tube current.

Figure 8:
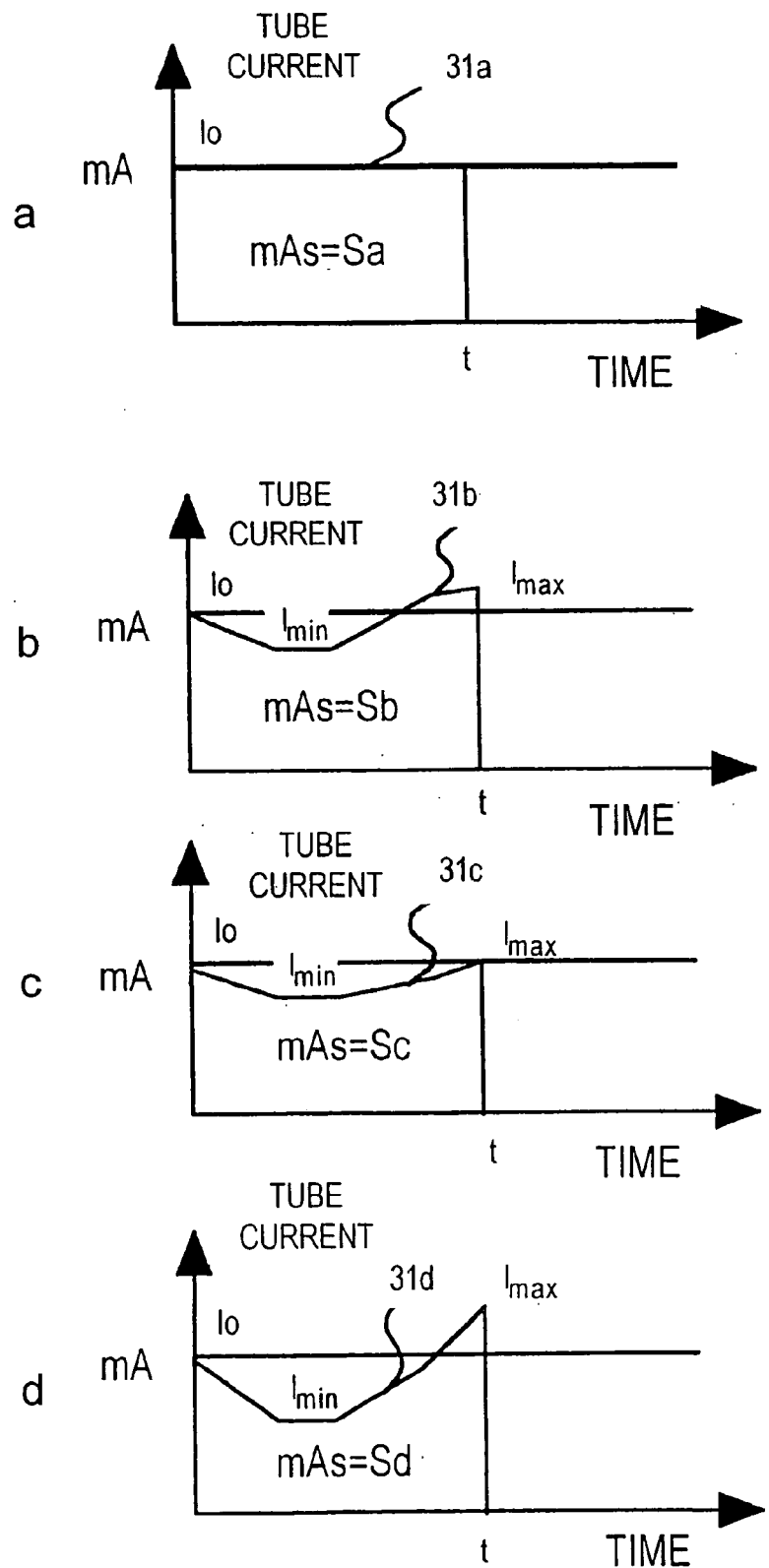
FIGS. 8a to 8b are graphs which show examples of the variation control pattern of the tube current.

FIGS. 8a to 8d illustrate examples of the variation control pattern of the tube current. The variation control pattern 31a of the tube current shown in FIG. 8(a) shows a usual example in which the tube current is constant ($I_0$), and the minimum value ($I_{min}$) and the maximum value ($I_{max}$) of the tube current are the same as $I_0$. The value of mAs is represented by the area Sa in the graph of the variation control pattern 31a of the tube current of FIG. 8a. Next, in a variation control pattern 31b of the tube current shown in FIG. 8b, the tube current is the same value $I_0$ as FIG. 8a at the initial time, becomes a minimum value $I_{min}$ lower than $I_0$ midway, and becomes a maximum value $I_{max}$, higher than $I_0$, close to the end. The value of mAs is represented by the area Sb in the graph of the variation control pattern 31a of the tube current of FIG. 8b, but this area Sb is smaller than the area Sa of FIG. 8a, and the exposure dose of the body being examined is reduced.

In a variation control pattern 31c of the tube current shown in FIG. 8c, the maximum value $I_{max}$ near the end of the scan is reduced, being closer to $I_0$ than in the graph of FIG. 8b. In this case, the amount of tube current over the entire scan is restrained so as to be somewhat lower. In the graph of the variation control pattern 31c of the tube current of FIG. 8c, the value of mAs is represented by an area Sc, but this area Sc is still smaller than the area Sb of FIG. 8b, and the exposure dose of the body being examined is further reduced.

In a variation control pattern 31d of the tube current shown in FIG. 8d, the minimum value $I_{min}$ of the middle period is further reduced, the difference with respect to $I_0$ being larger than in FIG. 8b. In the variation control pattern 31d of the tube current of FIG. 8(d), the value of mAs is represented by an area Sd, but the area Sd is still smaller than the area Sc of FIG. 8c.

When the maximum value of the tube current setting value is reduced, as in the case of FIG. 8c, the tube current is reduced in a thick portion of the body being examined, i.e., a portion where the X-ray passage is long. Accordingly, the variation control pattern 31c of the tube current of FIG. 8c is suitable for a case in which it is desirous to provide an image quality in the part of low density, such as the lungs, which is particularly desirable, and it is desired that the exposure dose in the areas of high density, such as the abdomen, be reduced.

When the minimum value of the tube current setting value is reduced, as in the case of FIG. 8d, the tube current is reduced in a thin portion of the body being examined, i.e., where the X-ray passage is short. Accordingly, the variation control pattern 31d of the tube current of FIG. 8d is suitable if high image quality in a part of high density, such as bone peripheral or parenchymatous tissue, and low exposure dose in areas of low density is particularly desired.

In FIGS. 8c and 8d, only the maximum value $I_{max}$ or the minimum value $I_{min}$ of the tube current setting value is reduced, but the exposure dose also can be reduced uniformly with respect to the entire area of the body being examined by reducing both the maximum value and the minimum value. With respect to the variation control pattern of the tube current set in this way, mAs is again calculated and is used as it is when it is judged that there is no problem.

Next, in the process of the scan in step 114, the operator executes the scan according to the scan conditions decided upon, including the variation control pattern of the tube current as determined above.

Next, in the process of display of the mAs integrated value in step 115, the integrated value of mAs during the scan is progressively calculated in accordance with the above-stated formula (5), and it is displayed in real time on the screen of the display device 25, so as to be presented to the operator. The mAs integrated value display method may involve display of a ratio with respect to the mAs value as a whole, or display of the absolute value of the integrated mAs. However, the relative value and the absolute value can be simultaneously displayed as well.

Figure 9A:
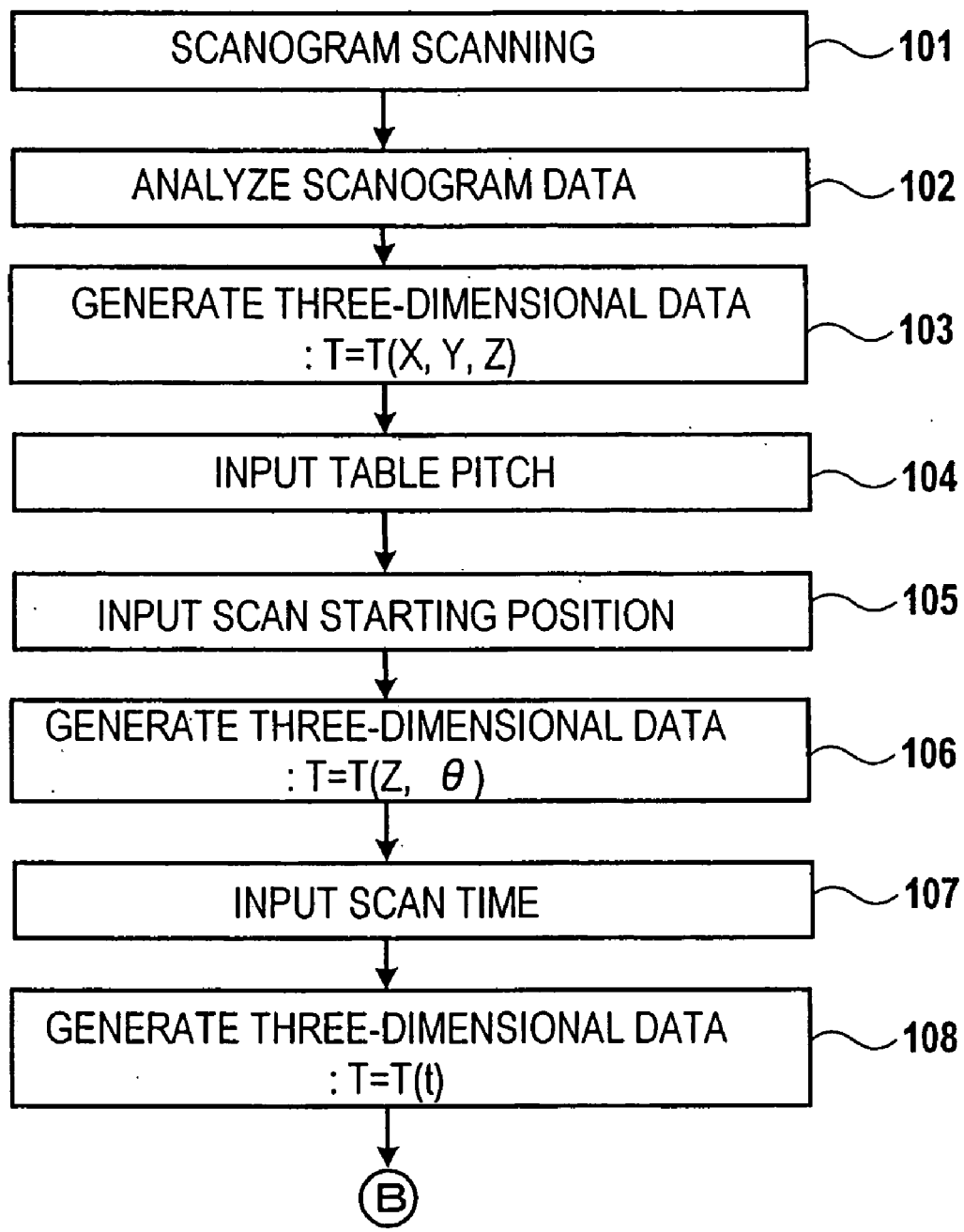
FIGS. 9a and 9b, when combined, comprise a flow chart of a series of operations of a second example of a scan operation using the X-ray CT device in accordance with the present invention.
Figure 9B:
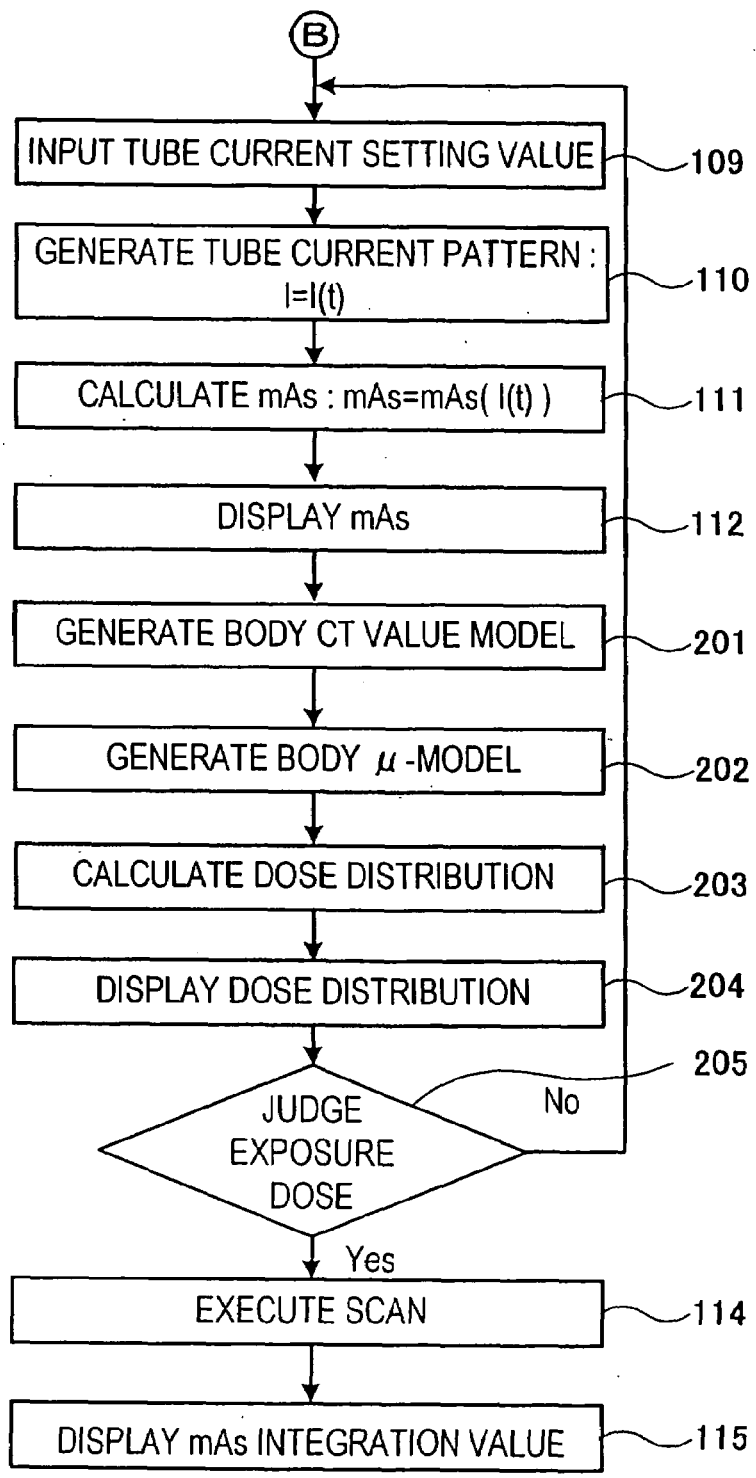

A second scan operation of the X-ray CT device in accordance with the present invention will be explained next. FIGS. 9a and 9b comprise a flow chart consisting of a series of operations which make up the second scan operation. In this scan operation, after the processes of the mAs calculation of step 111 and the mAs display of step 112, the processes of calculation and display of the dose distribution within the body being examined are added to the flow chart of the first scan operation of FIG. 3a and FIG. 3b, such that the operator can see the dose distribution within the body being examined and can better judge whether to execute the scan. Therefore, in the explanation of this operation, stress will be placed on the processes of calculation and display of the dose distribution within the body being examined in steps 201 to 205.

Figure 10:
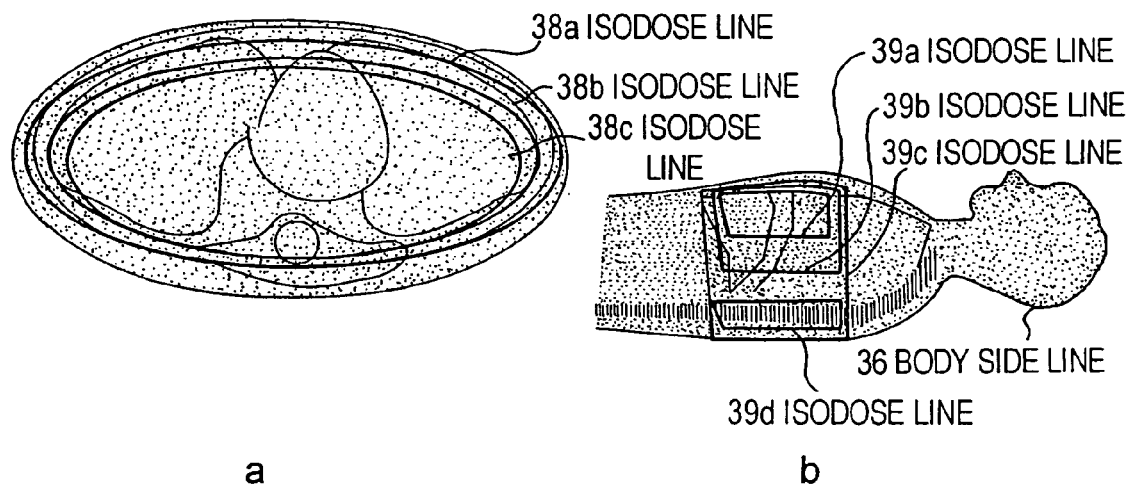
FIGS. 10a and 10b are diagrams of a displayed example of calculated dose distribution within the body being examined.

Steps 201 to 205 within the second scan operation of FIG. 9b will be explained next, but first, display examples of the calculating result of the dose distribution within the body being examined will be explained with reference to FIGS. 10a and 10b. FIG. 10a shows a display example of the dose distribution in a cross section 35 of the body being examined, and FIG. 10b shows a display example of the dose distribution on a side view 36 of the body being examined extending in the body axis direction. Both these figures show isodose lines 38a to 38c, 39a to 39c of the distribution dose within the body being examined, and the dose is increased at portions closer to the body surface. In this operation, the dose distribution of the body being examined is presented to the operator. Therefore, this operation has the distinctive feature which allows the operator to make a more detailed evaluation of the X-ray exposure of the body being examined.

In this operation, before the dose distribution within the body being examined is calculated in step 203, a CT value model of the body being examined is generated in step 201 and a µ-model of the body being examined is generated in step 202 as a preparation. Thereafter, the dose distribution within the body being examined is calculated on the basis of µ-model data of the body being examined and dose data of the X-ray irradiating the body being examined.

First, in the process of the CT value model generation of the body being examined in step 201, the CT value distribution model (hereinafter called a standard body CT value model) data of a standard human body is obtained in advance and stored in a storing means of the controller 20. The CT value model (hereinafter called a body CT value model) of the body being examined is obtained by correcting the standard human body CT value model data on the basis of the data of a scanogram image of the body being examined, as obtained in step 101. For example, three-dimensional CT value distribution data obtained from a CT-scanned cross-section image of a standard human body phantom, etc. is used as the above standard human body CT value model data. The cross-section image shows the distribution of the CT value and also shows the distribution of the linear attenuation coefficient of X-rays of energy actually used (normally 60 keV). Accordingly, the three-dimensional CT value distribution data obtained by three-dimensionally reconstructing this cross-section image is data of a three-dimensional spatial distribution of the linear attenuation coefficient, and it can be utilized to calculate the attenuation of the X-ray irradiating the body being examined.

One example of a method of generating the body CT value model will be explained with reference to FIGS. 11a to 11d. In this example, the body CT value model data showing the three-dimensional CT value distribution of the body being examined is generated from the actually measured scanogram image data obtained by scanning the body being examined in step 101, and the above-described standard human body CT value model data. In the generation of this body CT value model, the scanogram image data of the body being examined and the scanogram image data of the standard human body are utilized as media.

Figure 11:
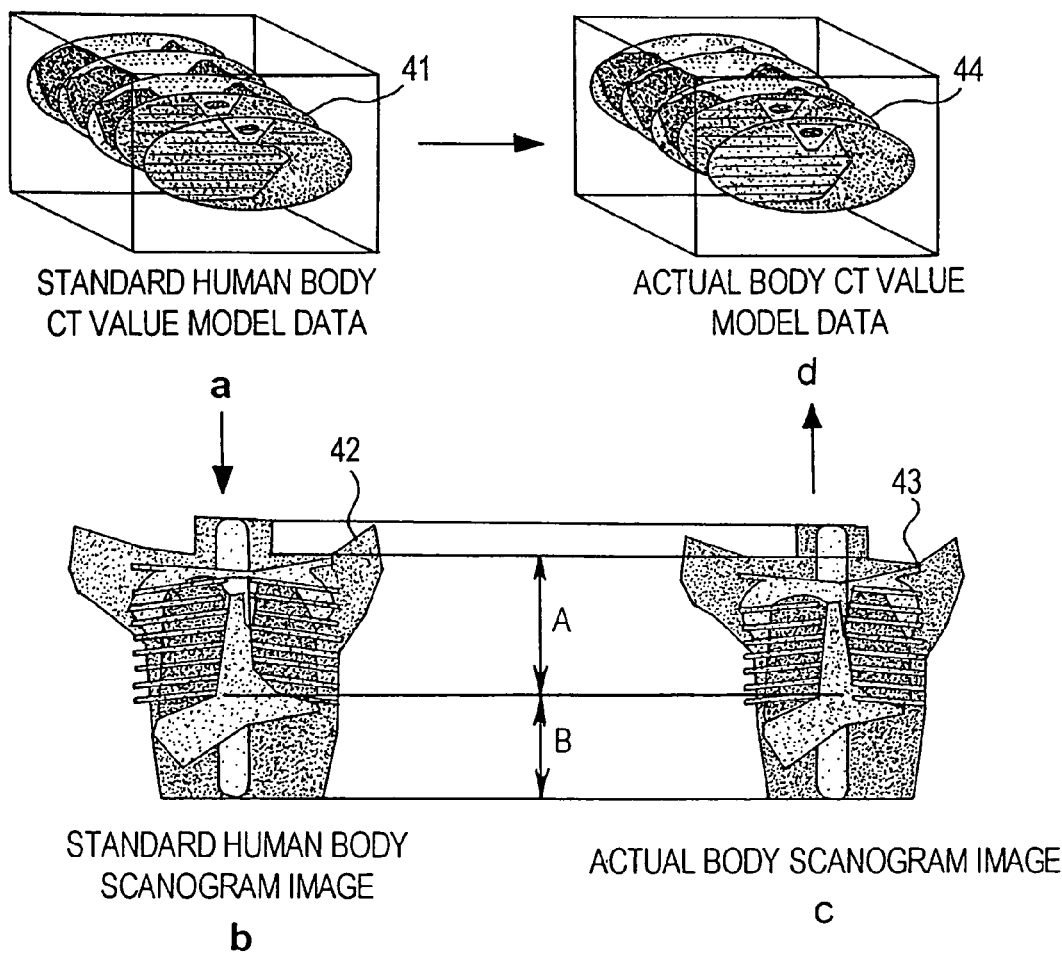
FIGS. 11a to 11d are diagrams illustrating the procedure for making a CT value model of a body being examined.

FIGS. 11a to 11d illustrate the production of the body CT value model in step 201. FIG. 11a shows an example of the standard human body CT value model data 41, and FIG. 11b shows an example of the scanogram image data 42 of the standard human body calculated from the standard human body CT value model data 41 of FIG. 11a. FIG. 11c shows an example of the actually measured scanogram image data 43 of the body being examined, and FIG. 11d shows an example of the calculated body CT value model data 44. The standard human body CT value model data 41 of FIG. 11a shows the CT value distribution model of a trunk portion of the standard human body, such as a human body phantom, etc., and shows the CT value distribution model of cross-sections from the shoulder to the abdomen.

The scanogram image can be generated by a calculation based on the three-dimensional CT value distribution model. Accordingly, the standard human body scanogram image data 42 of FIG. 11b is obtained by calculating the projection of the standard human body CT value model data 41 of FIG. 11a toward the front of the body. The actually measured scanogram image data 43 of the body of FIG. 11c consists of scanogram image data obtained by scanning, from the front, the body being examined at the same trunk portion as the standard human body scanogram image data 42. This image is hereinafter called a body scanogram image.

FIGS. 11b and 11c show the standard human body scanogram image data 42 of the body trunk portion and the actual body scanogram image data 43 aligned with each other. However, the standard human body scanogram image data 42 and the actual body scanogram image data 43 are usually different from each other in size and CT values. Therefore, the standard human body scanogram image data 42 and the actual body scanogram image data 43 are compared with each other, and matching portions of the standard body scanogram image are set as they are and portions of the standard body scanogram image which are different from the actual scanogram image are deformed on the basis of the difference between both data, so that the standard human body CT value model data 41 will conform to the body being examined, and then the body CT value model data 44 is generated.

In the example of the body trunk portion as seen in FIGS. 11b and 11c, the body trunk portion is first divided into a length A from the shoulder to the diaphragm and a length B from the diaphragm to the intestinal tract in the standard human body scanogram image data 42 and the actual body scanogram image data 43 with respect to the body axis direction. The standard human body CT value model data 41 is extended by interpolating cross-sections, or shortened by thinning out cross-sections, based on differences between the two, so that the CT value distribution of the standard human body CT value model data 41 in its body axis direction is close to the actual structure of the body being examined. With respect to the leftward and rightward directions, the body trunk portion is similarly divided into left and right portions, with the body axis serving as a reference, and left and right spreads are corrected on the basis of the respective differences so as to be close to the actual structure of the body being examined. Data in the directions toward the front and back of the body in the standard human body CT value model data 41 is linearly interpolated on the basis of the X-ray passage length in the forward and backward directions presumed from the actual body scanogram image data 43. Thus, the body CT value model data 44 is generated by conforming the standard human body CT value model data 41 to the real body being examined on the basis of the two scanogram image data 42, 43.

Next, in the body μ-model generation of step 202, the CT values of the body CT value model data 44 generated in step 201 are converted to linear attenuation coefficients μ, and a three-dimensional μ-value distribution model of the body being examined is generated. The conversion from the CT value to the linear attenuation coefficient μ is performed as follows.

The CT value is determined by the linear attenuation coefficient with respect to X-rays of actual operating energy (60 keV is normally used), and it is defined as water=0, air=1000 and average bone=1000. When the CT value in the position X of the body CT value model is now set to $CT_x$, the linear attenuation coefficient $\mu_x$ for actual operating energy (60 keV) in this position X is given by the following formulas (6) and (7).

$$\mu_x = CT_x(\mu_w - \mu_{air})/1000 + \mu_w (\text{here, } CT_x \leq 0.0) \quad (6)$$

$$\mu_x = CT_x(\mu_{bone} - \mu_w)/1000 + \mu_w (\text{here, } CT_x > 0.0) \quad (7)$$

Here, $\mu_w$ is the linear attenuation coefficient (=0.206 cm$^{-1}$) of water, and $\mu_{air}$ is the linear attenuation coefficient (=0.00025 cm$^{-1}$) of the air, and $\mu_{bone}$ is the linear attenuation coefficient (=0.567 cm$^{-1}$ in the case of density 1.8 g/cm$^3$) of bone.

Next, in the process of the dose distribution calculation in step 203, as shown in FIGS. 12a to 12c, the dose distribution (FIG. 12c) within the body being examined is calculated by using the data calculated in step 111 (FIG. 12a) representing the amount of X-rays entering the body being examined and body p-model data 45 (FIG. 12b) calculated in step 202. In the calculation of this step 203, attenuation of the X-rays within the body being examined is calculated and a spatial distribution of the dose within the body is calculated in consideration of the energy spectrum of the X-rays irradiating the body. When the X-rays irradiate the body from an arbitrary direction, the attenuation of the X-rays can be analytically calculated by using the body μ-model data in the model of the three-dimensional linear attenuation coefficient (μ) of the body being examined. Such a calculating technique is already used in other fields, e.g., radiation treatment planning devices (reference I: Kiyonari INAO, Radiation Treatment Planning Systems pp. 90 to 92, pp. 113 to 115, Shinohara Publishing, April 20, Heisei 4(1992)).

In the calculation of the attenuation of the X-rays, a transmitting effective distance δ of the X-rays from the position to be examined X in the body to the X-ray source 12 is first calculated. The unit of distance is defined to be the distance of attenuation of the X-rays to 1/e through the medium. When the energy spectrum of the X-rays is not considered, the effective distance δ is represented by the following formula (8), wherein the medium of the composition i is $d_i$ (cm) in real distance and the linear attenuation coefficient of the composition i is $\mu_i$ (cm$^{-1}$) from the position being examined X to the X-ray source 12.

$$\delta = \Sigma \mu_i \cdot d_i \quad (8)$$

However, when the energy spectrum of the X-rays is considered, the effective distance becomes a value different in accordance with the energy of the X-rays. When the linear attenuation coefficient of the composition i with respect to energy j of the X-rays is $\mu_{ij}$ (cm$^{-1}$), the effective distance $\delta_j$ with respect to energy j of the X-rays is represented by the following formula (9).

$$\delta = \Sigma \mu_{ij} \cdot d_j \quad (9)$$

Here, $\mu_{ij}$ is the linear attenuation coefficient (cm$^{-1}$) of the composition i with respect to X-rays of energy j, and $d_i$ is the distance (cm) of the X-ray passage within the composition i. It is necessary to calculate $\mu_{ij}$ from the μ-value model of the body being examined in accordance with the energy j of the X-rays.

Next, the dose in the position to be examined X in the body is calculated. The distance from the X-ray source 12 to the position to be examined X is set to $r_x$ (m), and the dose at a distance of 1 m is set to $I_0$ (C/Kg: C is coulomb). For example, $I_0$ may be experimentally calculated. Where the energy spectrum of the X-rays, i.e., the relative proportion of the energy components j is $S_j$, the dose $I_x$ (C/kg) in the position to be examined X is represented by the following formula (10).

$$I_x = \sum_j S_j \cdot I_0 \cdot \exp(-\delta_j)/r_x^2 \quad \text{(unit: C/kg)} \tag{10}$$

Here, $I_0$ is the dose (the dose in the air at the unit distance from the X-ray source 12), and $r_x$ is the distance from the X-ray source 12 to the position to be examined X (unit m), and $S_j$ is the energy spectrum of the X-rays.

As a result of the calculation using the formula (10), the dose at an arbitrary position X within the body being examined is calculated when the X-ray source 12 is located in a certain position $Q(Z,\theta)$. The dose at position X in one rotation of the X-ray source 12 is obtained by rotating the position $Q(Z,\theta)$ of the X-ray source 12 around the body being examined, and integrating the dose over one rotation ($\theta=0$ to $2\pi$). The dose distribution within the body being examined in the slice position Z can be calculated by making this calculation for each set position within the body in the above-described procedure. Further, the dose distribution in other slice positions can be similarly calculated. Accordingly, the three-dimensional dose distribution within the body being examined is obtained by calculating doses at cross-sections over the entire area of the scanning with respect to the axis of the body.

When the image of one cross-section is scanned (two-dimensional case), the distribution of the dose within the body being examined can be precisely calculated by the above-described calculation. However, when the CT-photograph of plural cross-sections is taken during one scan (three-dimensional case), there is a fear that the calculating accuracy is reduced when scattering of the X-rays during the scan is considered. Since the energy of the X-rays is on the order of 100 KeV or less in the X-ray CT device, it is sufficient to consider only the Compton scattering when estimating the scattering rays (see reference 1). The calculating accuracy can be further raised by considering this Compton scattering.

The calculated three-dimensional dose distribution of the body being examined is obtained by calculating the dose at each set point in each position within the body by the above procedure. The calculated dose distribution of the body being examined is temporarily stored in the controller 20, and it is displayed in a figure easily understood by an operator, etc., e.g., the figure shown in FIGS. 10a and 10b.

Next, in the dose distribution display in step 204, the result of step 203 is displayed in the display device 25. Display examples in this embodiment include the dose distribution displayed within a cross-section 35 (FIG. 10a), or the dose distribution of a side face 36 (FIG. 10b). In these figures, internal organs of the body being examined and isodose lines showing the dose distribution, etc. are displayed in cross-section. Accordingly, the exposure dose of each internal organ can be recognized at a glance, and the X-ray exposure to the body being examined can be better evaluated.

Next, in the process of the exposure dose judgment in step 205, the operator sees the calculated dose distribution displayed in step 204, and determines whether there is no danger that the X-ray exposure to the internal organs within the body will be excessive. When the judgment is Yes, the operator proceeds to the scan execution of step 114, and the scan is started. In contrast to this, when the judgment is No, the operation goes back to the tube current setting value input in step 109, the tube current setting value is revised, and the tube current pattern is reevaluated.

The method for generating the CT value model data of the body being examined in step 201 may employ CT scanning data of the same body that has been scanned in the past, this procedure being executed instead of the method for using the standard human body CT value model data. In this case, since the CT value distribution data of the same body is actually used, there is an advantage in that correction of the shape of the standard human body CT value model data 41 is not required. However, since this is not usable for a first time CT scanning, for a body which has been CT-scanned in the past, a model is made using the second or subsequent CT scans.

The operator can estimate the dose distribution in advance by simulation-calculating the dose distribution within the body before the CT scan, and displaying the result, for example as shown in FIGS. 10a and 10b.

Thus, it is possible to perform a detailed setting in which the exposure dose is not simply uniformly reduced with respect to the entire tissue of the body being examined, but is particularly reduced with respect to the tissue of high radiation sensitivity, such as bone marrow, the lungs, etc., and the level of the exposure dose in the tissue of relatively low radiation sensitivity, such as fat, muscles, etc., on the other hand, is raised to the extent that the image quality can be sufficient.

Figure 12:
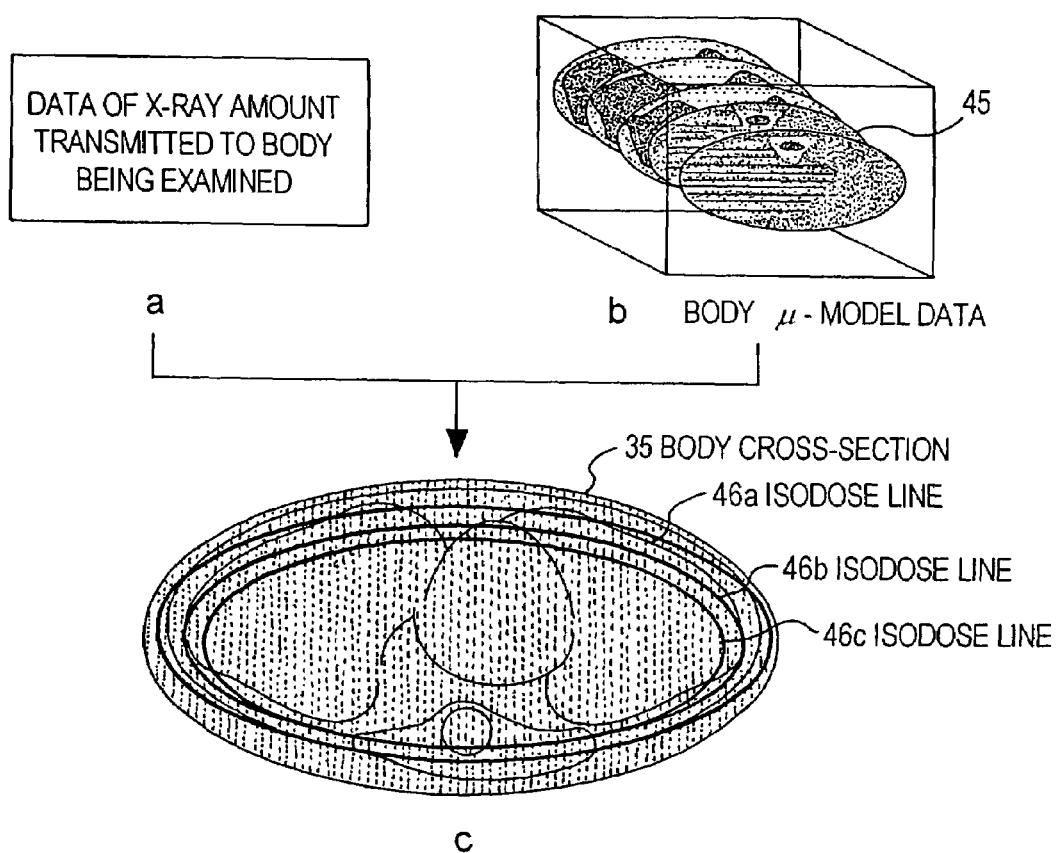
FIGS. 12a to 12c are diagrams which illustrate the procedure for calculation of X-ray irradiation distribution.
Figure 13:
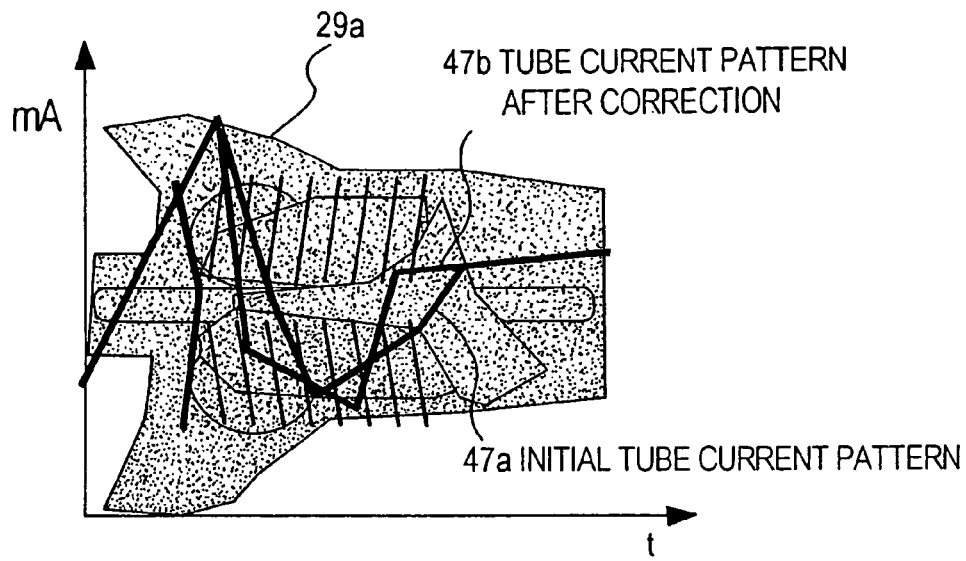
FIG. 13 is a diagram which shows a display example in which the variation control pattern of the tube current is superposed on the scanogram image of the body being examined.

Next, an example of editing the variation control pattern of the tube current for CT-scanning the body being examined will be explained with reference to FIG. 13. In FIG. 13, the variation control pattern of the tube current is superposed on the scanogram image of the body being examined. In FIG. 12, scanogram image data 29a consists of data of the body trunk portion, and the variation control patterns of the tube current are the initial variation control pattern 46a of the tube current before the editing, and the corrected variation control pattern 46b of the tube current after the editing.

In the editing of this variation control pattern of the tube current, the variation control pattern 46a of the tube current initially set and displayed over the scanogram image 29a on the screen of the display device 25 is edited by adding a correction using the operating means 21 based on the scanogram image data 29a, or in certain cases based on the irradiation dose distribution within the body being examined, to obtain a new variation control pattern 46b of the tube current. The variation control pattern of the tube current of a particular portion is reset by this editing operation.

In this editing operation, for example, the tube current is set to an average value in an area with great changes in density, such as in the vicinity of the diaphragm, in automatic setting of the variation control pattern of the tube current. However, the tube current is set high in an area where the image quality is needed, even if this means an increased exposure dose. If the scan condition is set as mentioned above, the variation control pattern of the tube current becomes a function of only time t, so that the value of the tube current at an arbitrary time can be changed. In the example of FIG. 13, the variation control pattern 46a of the tube current in the initial period is changed to the variation control pattern 46*b* of the tube current, slightly reducing the tube current in the area of the lungs and slightly increasing the tube current in the area of the diaphragm.

Figure 14:
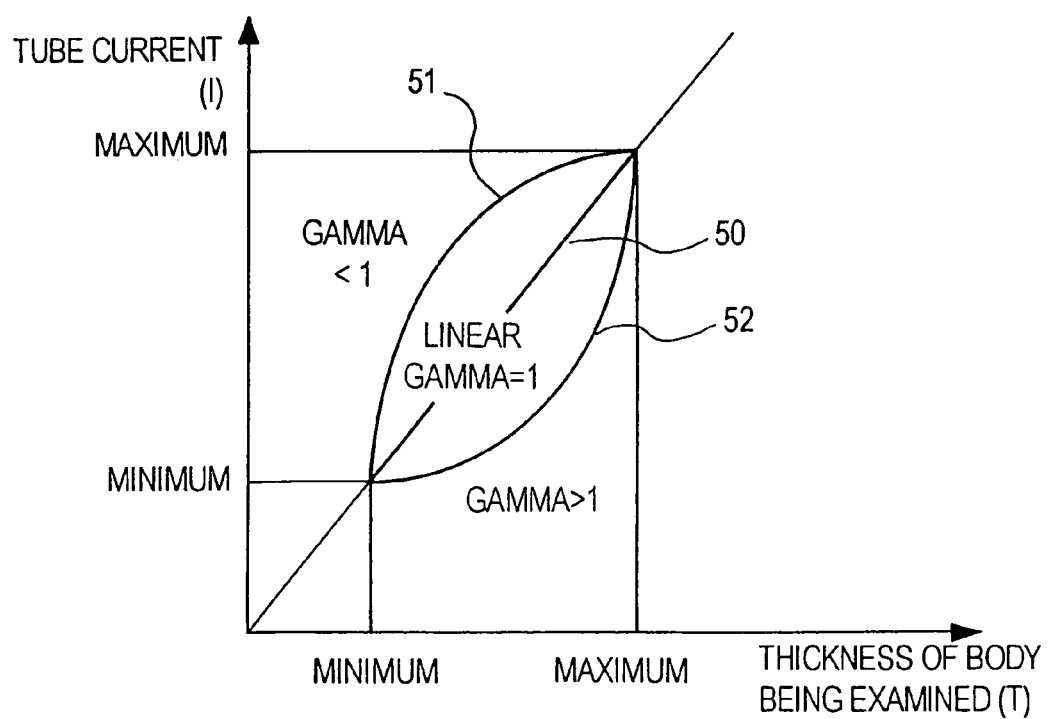
FIG. 14 is a graph showing the relation of the tube current and the thickness of the body being examined.

FIG. 14 is a view showing the relation between the tube current and the thickness (corresponding to the X-ray passage length) of the body being examined. In the above explanation of the process of step 110, the maximum value and the minimum value of the tube current are matched with the maximum value and the minimum value of the thickness of the body being examined, so that a linear relation is formed between the tube current and the thickness of the body. However, with respect to the relation between the tube current and the thickness of the body being examined, it is possible to form a nonlinear relation by setting the operator differently. The relation of the tube current I and the thickness T of the body being examined, as shown in FIG. 14, is represented by the following formula (11).

$$I - I_{min} = K(T - T_{min})^\gamma$$

Here, $K = (I_{max} - I_{min})/(T_{max} - T_{min})^\gamma$ \quad (11)

where, $I_{max}$ and $I_{min}$ are the maximum value and the minimum value of the tube current, respectively, and $T_{max}$ and $T_{min}$ are the maximum value and the minimum value of the thickness of the body being examined, respectively, and γ is a constant. γ is hereinafter called gamma.

In FIG. 14, graph 50 shows the case of gamma=1, wherein the relation of the tube current and the thickness of the body being examined is linear. Graph 51 shows the case of gamma<1, and graph 52 shows the case of gamma>1. In the graphs 51 and 52, the relation of the tube current and the thickness of the body being examined is nonlinear. In the case of FIG. 14, the relation of the tube current and the thickness of the body being examined is determined by the value of gamma. Accordingly, as shown in FIG. 14, the relation of the tube current I and the thickness T of the body being examined can be changed by employing a formula, such as the formula (11), and inputting the value of gamma into the device through the operating means 21. Further, in the real operation, for example, the maximum value and the minimum value of the tube current are matched to the maximum value and the minimum value of the thickness of the body being examined, so that a linear relation is formed in the initial setting, and the operator performs no special setting thereafter. The nonlinear relation can be formed when the operator inputs gamma. In FIG. 14, a change of gamma to be >1 is considered when reduction in exposure of the body has priority, and the change of gamma to be <1 is considered when the image quality has priority.

As explained above, the X-ray CT device of the present invention includes operating means for setting the scan conditions of the device, scanogram analyzing means for generating the three-dimensional X-ray passage length model of the body being examined from the scanogram image data of the body, tube current setting means for automatically setting the variation control pattern of the tube current for the part of the body to be scanned based on the scan conditions and the three-dimensional X-ray passage length model of the body, and dose calculating means for calculating and displaying the dose which will be given to the body being examined on the basis of the variation control pattern of the tube current. Accordingly, the variation control pattern of the tube current, during the scan, can be automatically set by inputting the maximum value and the minimum value of the tube current as scan conditions, and the X-ray exposure to the body being examined can be also evaluated. Further, when there is a fear that the X-ray exposure to the body being examined will be excessive, the variation control pattern of the tube current can be reset.

Further, the X-ray CT device of the present invention has dose distribution calculating means for calculating and displaying the dose distribution within the body to be examined on the basis of the variation control pattern of the tube current to be applied during the scan and the three-dimensional CT value model data of the body being examined, which has been generated in advance. Accordingly, the dose distribution within the body to be CT scanned can be known in advance. Thus, it is possible to judge whether the scan should be executed or not in consideration of the degree of the X-ray exposure of the internal organ concerned.

Further, the X-ray CT device of the present invention has means for generating a CT value model of the body being examined on the basis of the standard human body CT value model data obtained e.g. by CT-scanning a human body phantom, and the scanogram image data of the body being examined. Accordingly, the body CT value model data also can be generated by obtaining only one preliminary scanogram of the body being examined in cases where no CT scan has been made previously.

Further, in the X-ray CT device of the present invention, the scanogram image of the body being examined and the variation control pattern of the tube current are displayed next to each other, or are overlapped, on the same area of a display means. Accordingly, the operator can edit the variation control pattern of the tube current while viewing the part of the body to be scanned, so that the tube current suitable for the part to be scanned can be easily set.

The invention claimed is:

1. An image display method of operation of an X-ray CT device comprising a step of obtaining a scanogram image used to obtain a cross-section image of the body being examined, and displaying this scanogram image in a display device, a step of calculating the length of the passage of X-rays through the body being examined on the basis of the scanogram image including calculating the X-ray passage length from the amount of X-rays to which the body will be exposed and standard human body model data, a step of displaying a control pattern of a variation of a first supply of electric current to an X-ray source so as to match with the displayed scanogram image, a step of performing through operating means an editing operation on the control pattern of the variation of the first supply of electric current to obtain another control pattern of variation of a second supply of electric current based on this scanogram image, and a step of obtaining the cross-section image of the body being examined on the basis of the another control pattern of the variation of the second supply of electric current and displaying this cross-section image in display means.

2. An X-ray CT device comprising an X-ray source for transmitting X-rays to a body being examined, a high voltage generator supplying a high voltage electric current to the X-ray source, an X-ray detector arranged opposite to the X-ray source with respect to the body being examined for detecting the amount of X-rays passing through the body being examined, scan condition setting means for setting conditions for a scan to obtain a cross-section image of the body, scanogram image collecting means for obtaining a scanogram image of the body being examined, display means for displaying the obtained scanogram image, scanning position setting means for using the displayed scanogram image to set the position for scanning a cross-section, cross-section image reconstructing means transmitting X-rays from the X-ray source while rotating the X-ray source around the body being examined according to the set scan conditions including the scanning position, and reconstructing the cross-section image from the data of X-ray passage through the body being examined as detected by the X-ray detector, and control means for causing the reconstructed cross-section image to be displayed by the display means; characterized in that the X-ray CT device further comprises passage length calculating means for calculating the length of the passage of X-rays through the body being examined on the basis of the scanogram image, the passage length calculating means calculating the X-ray passage length from the amount of X-rays to which the body will be exposed and standard human body model data, and electric current setting means for setting an electric current value to the high voltage generator for generating in the X-ray source X-rays adjusted according to the part of the body being scanned based on the calculated X-ray passage length and the scan conditions.

3. The X-ray CT device according to claim 2, wherein said electric current value setting means determines a first electric current value based on the scan conditions and sets this value in the high voltage generator.

4. The X-ray CT device according to claim 2, wherein said electric current value setting means determines the maximum value and the minimum value of a second electric current value for each part of the body being examined based the X-ray passage length and sets this value in the high voltage generator.

5. The X-ray CT device according to claim 2, wherein said electric current value setting means calculates a first electric current value based on the scan conditions, and calculates a second electric current value for each part of the body being examined from this first electric current value and the X-ray passage length at this part of the body, and sets this second electric current value in the high voltage generator.

6. The X-ray CT device according to claim 2, wherein said electric current value setting means sets the gamma value of the curve of the relation between the X-ray passage length and the electric current value supplied to the X-ray source characterizing the values for each part of the body being scanned, and sets electric current values derived from this gamma value in the high voltage generator.

7. The X-ray CT device according to claim 2, wherein said control means displays a control pattern of variation of the electric current value for each part of the body being examined and the scanogram image of the body being examined next to each other, or overlaps the variation control pattern on the scanogram image.

8. An X-ray CT device comprising an X-ray source for transmitting X-rays to a body being examined, a high voltage generator for supplying a high voltage electric current to the X-ray source, an X-ray detector arranged opposite to the X-ray source with regard to the body being examined for detecting the amount of X-rays passing through the body, scan condition setting means for setting scan conditions for obtaining a cross-section image of the body, scanogram image collecting means for obtaining a scanogram image of the body being examined, display means for displaying the obtained scanogram image, scanning position setting means for setting the position of the cross-section to be scanned on the displayed scanogram image, condition setting means for setting the scan conditions of a CT scanner, cross-section image reconstructing means for transmitting the X-ray from the X-ray source while rotating the X-ray source to various positions around the body being examined, including the scanning positions which have been set, and reconstructing the cross-section image from the X-ray body passage data detected by the X-ray detector, and control means for causing the reconstructed cross-section image to be displayed on the display means; characterized in that the X-ray CT device further comprises passage length calculating means for calculating the length of the passage of X-rays through the body being examined on the basis of the scanogram image, the passage length calculating means calculating the X-ray passage length from the amount of X-rays to which the body will be exposed and standard human body model data, and dose calculating means for calculating the dose to be received in each part of the body to be scanned, based on the size of the electric current for generating X-rays in the X-ray source, the calculated X-ray passage length, and the scan conditions, and the control means causes the calculated dose to be displayed next to the scanogram image or to overlap a graph of the calculated dose on the scanogram image in the display means.

9. An X-ray CT device comprising an X-ray source for transmitting X-rays to a body being examined, a high voltage generator for supplying a high voltage electric current to the X-ray source, an X-ray detector arranged opposite to the X-ray source with respect to the body being examined for detecting the amount of X-rays passing through the body being examined, scan condition setting means for setting scan conditions for obtaining a cross-section image of the body, scanogram image collecting means for obtaining a scanogram image of the body being examined, display means for displaying the obtained scanogram image, scanning position setting means for setting the position of the cross-section to be scanned on the displayed scanogram image, condition setting means for setting the scan condition of the CT scanner, cross-section image reconstructing means for transmitting the X-rays from the X-ray source while rotating the X-ray source at positions around the body being examined, including the scanning positions which have been set, and for reconstructing the cross-section image from the X-ray body passage data detected by the X-ray detector, and control means for causing the reconstructed cross-section image to be displayed on the display means; characterized in that the X-ray CT device further comprises passage length calculating means for calculating the length of the passage of X-rays through the body being examined on the basis of the scanogram image, the passage length calculating means calculating the X-ray passage length from the amount of X-rays to which the body will be exposed and standard human body model data, and dose calculating means for calculating the dose resulting from the electric current value for generating in the X-ray source X-rays corresponding to the part of the body being scanned and calculated from the calculated X-ray passage length and the scan conditions, and the control means causes the calculated dose distribution to be displayed next to the scanogram image, or overlaps a graph of the calculated dose distribution on the scanogram image, in the display means.

10. An X-ray CT device characterized in that it comprises a high voltage generator for supplying a high voltage electric current to an X-ray source for transmitting X-rays to a body being examined, an X-ray detector arranged opposite to the X-ray source with respect to the body being examined for detecting X-rays passing through the body being examined, scanner driving means for rotating and operating a scanner for rotating the X-ray source and the X-ray detector around the body being examined, operating means for setting scan conditions for obtaining a cross-section image of the body, scanogram analyzing means for obtaining a scanogram image of the body being examined, analyzing this scanogram image, and calculating the length of the passage of X-rays through the body being examined from the amount of X-rays to which the body will be exposed and standard human body model data, electric current setting means for determining an electric current value based on the scan condition and the X-ray passage length and setting the value in the high voltage generator, a controller for making the X-ray source transmit X-rays according to the electric current values which have been set while making the scanner driving means rotate the scanner and collecting data for obtaining the cross-section image of the body being examined, an image processor for reconstructing the cross-section image by reconstructing the collected data, and a display device for displaying the reconstructed cross-section image.

11. An image display method of operation of an X-ray CT device comprising a step of setting scan conditions, including the supply of electric current to an X-ray source, for obtaining a cross-section image of a body being examined, a step of obtaining a scanogram image of the body being examined and displaying this scanogram image in display means, a step of analyzing the displayed scanogram image, a step of calculating the length of the passage of X-ray through the body being examined on the basis of the scanogram image including calculating the X-ray passage length from the amount of X-rays to which the body will be exposed and standard human body model data, a step of calculating the electric current pattern for each part of the body being scanned from the electric current supplied to the X-ray source and the calculated X-ray passage length of the body being examined, and a step of setting electric current values based on the calculated electric current control pattern in a high voltage generator, supplying the electric current generated by the high voltage generator to the X-ray source, and obtaining the cross-section image of the body being examined from settings of that electric current and the scan conditions, and displaying this cross-section image in a display device.

12. The image display method of operation of the X-ray CT device according to claim 11, wherein the control pattern of variation of the electric current value set for each part of the body being examined and the scanogram image of the body being examined are arranged next to each other or are overlaid in the display step.

13. An image display method of operation of an X-ray CT device comprising a step of setting scan conditions, including electric current supplied to an X-ray source, for obtaining a cross-section image of a body being examined, a step of obtaining a scanogram image of the body being examined and displaying this scanogram image in display means, a step of analyzing the displayed scanogram image, a step of calculating the length of the passage of X-rays through the body being examined on the basis of the scanogram image including calculating the X-ray passage length from the amount of X-rays to which the body will be exposed and standard human body model data, a step of calculating the electric current control pattern for each part of the body to be scanned and the dose distribution within the body, based on the electric current supplied to the X-ray source and the X-ray passage length data of the body being examined, and a step of determining an electric current value based on the calculated electric current control pattern and the dose distribution within the body being examined, setting this value in a high voltage generator, supplying the electric current generated by the high voltage generator to the X-ray source, and obtaining the cross-section image of the body being examined based on that electric current and the scan conditions, and displaying this cross-section image in a display device.

14. The image display method of the X-ray CT device according to claim 13, wherein the control pattern of variation of the electric current value set for each part of the body being examined, the dose distribution within the body being examined, and the scanogram image of the body being examined are arranged next to each other, or are overlaid, in the above display step.

\* \* \* \* \*